US006652561B1

(12) United States Patent
Tran

(10) Patent No.: US 6,652,561 B1
(45) Date of Patent: Nov. 25, 2003

(54) METHOD AND APPARATUS FOR ATTACHING CONNECTIVE TISSUES TO BONE USING A PERFORATED SUTURE ANCHORING DEVICE

(75) Inventor: Minh Tran, Fountain Valley, CA (US)

(73) Assignee: Opus Medical, Inc, San Juan Capistrano, CA (US)

( * ) Notice: Subject to any disclaimer, the term of this patent is extended or adjusted under 35 U.S.C. 154(b) by 46 days.

(21) Appl. No.: 09/687,185

(22) Filed: Oct. 13, 2000

(51) Int. Cl.[7] .................................................. A61B 17/04
(52) U.S. Cl. .......................................... 606/232; 606/72
(58) Field of Search ........................... 606/232, 60, 72, 606/228, 75, 74, 233, 73

(56) References Cited

U.S. PATENT DOCUMENTS

| 3,143,916 A | 8/1964 | Rice |
| 4,301,551 A | 11/1981 | Dore et al. |
| 4,467,478 A | 8/1984 | Jurgutis |
| 4,483,023 A | 11/1984 | Hoffman, Jr. et al. |
| 4,590,928 A | 5/1986 | Hunt et al. |
| 4,597,776 A | 7/1986 | Ullman et al. |
| 4,605,414 A | 8/1986 | Czajka |
| 4,672,957 A | 6/1987 | Hourahane |
| 4,712,542 A | 12/1987 | Daniel et al. |
| 4,721,103 A * | 1/1988 | Freedland ................. 128/92 |
| 4,772,286 A | 9/1988 | Goble et al. |
| 4,823,780 A | 4/1989 | Odensten et al. |
| 5,195,542 A | 3/1993 | Gazielly et al. |
| RE34,293 E | 6/1993 | Goble et al. |
| 5,275,176 A | 1/1994 | Chandler |
| 5,330,468 A | 7/1994 | Burkhart |
| 5,336,240 A * | 8/1994 | Metzler et al. ............ 606/232 |
| 5,417,691 A | 5/1995 | Hayhurst |
| 5,441,508 A | 8/1995 | Gazielly et al. |
| 5,472,452 A | 12/1995 | Trott |
| 5,480,403 A | 1/1996 | Lee et al. |
| 5,501,683 A | 3/1996 | Trott |
| 5,501,695 A | 3/1996 | Anspach, Jr. et al. |
| 5,534,012 A | 7/1996 | Bonutti |
| 5,549,630 A | 8/1996 | Bonutti |
| 5,569,305 A | 10/1996 | Bonutti |
| 5,569,306 A | 10/1996 | Thal |
| 5,573,548 A | 11/1996 | Nazre et al. |
| 5,575,801 A | 11/1996 | Habermeyer et al. |
| 5,584,839 A | 12/1996 | Gieringer |
| 5,584,862 A | 12/1996 | Bonutti |
| 5,591,207 A | 1/1997 | Coleman |
| 5,658,313 A | 8/1997 | Thal |
| 5,665,110 A | 9/1997 | Chervitz et al. |
| 5,665,112 A | 9/1997 | Thal |
| D385,352 S | 10/1997 | Bales et al. |
| 5,681,333 A | 10/1997 | Burkhart et al. |
| 5,683,418 A | 11/1997 | Luscombe et al. |
| 5,683,419 A | 11/1997 | Thal |

(List continued on next page.)

Primary Examiner—Michael J. Milano
Assistant Examiner—Jessica R Baxter
(74) Attorney, Agent, or Firm—Stout, Uxa, Buyan & Mullins, LLP; Donald E. Stout

(57) ABSTRACT

A bone anchor device for attaching connective tissue to bone comprises an anchor body, a plurality of suture retaining apertures disposed in the anchor body, and deployable structure for securing the anchor body in bone. A longitudinal axis is disposed along a center of the anchor body, wherein the plurality of suture retaining apertures are spaced axially relative to one another. Additionally, in preferred embodiments, at least two of the plurality of suture retaining apertures are transversely offset from one another relative to the longitudinal axis, in staggered relation. Preferably, the deployable structure comprises a pair of deployable flaps. The anchor body comprises a substantially planar surface in which the plurality of suture retaining apertures are disposed. In its presently preferred embodiment, the anchor body comprises opposing substantially flat surfaces, wherein the plurality of suture retaining apertures extend through the entire anchor body. A stem extends proximally from a proximal end of the anchor body. At least a portion of a longitudinal slit is disposed in the stem.

21 Claims, 19 Drawing Sheets

U.S. PATENT DOCUMENTS

| | | | |
|---|---|---|---|
| 5,690,649 A | 11/1997 | Li | |
| 5,697,950 A | 12/1997 | Fucci et al. | |
| 5,707,362 A | 1/1998 | Yoon | |
| 5,707,394 A | 1/1998 | Miller et al. | |
| 5,709,708 A | 1/1998 | Thal | |
| 5,720,765 A | 2/1998 | Thal | |
| 5,728,136 A | 3/1998 | Thal | |
| 5,733,307 A | 3/1998 | Dinsdale | |
| 5,782,864 A * | 7/1998 | Lizardi | 606/232 |
| 5,782,865 A | 7/1998 | Grotz | |
| 5,797,963 A | 8/1998 | McDevitt | |
| 5,810,854 A | 9/1998 | Beach | |
| 5,814,071 A | 9/1998 | McDevitt et al. | |
| 5,860,978 A | 1/1999 | McDevitt | |
| 5,868,789 A | 2/1999 | Huebner | |
| 5,879,372 A | 3/1999 | Bartlett | |
| 5,882,340 A | 3/1999 | Yoon | |
| 5,891,168 A | 4/1999 | Thal | |
| 5,893,850 A | 4/1999 | Cachia | |
| 5,948,001 A | 9/1999 | Larsen | |
| 5,957,953 A | 9/1999 | DiPoto et al. | |
| 5,961,530 A | 10/1999 | Moore et al. | |
| 5,993,459 A | 11/1999 | Larsen et al. | |
| 6,007,567 A | 12/1999 | Bonutti | |
| 6,013,083 A | 1/2000 | Bennett | |
| 6,017,346 A * | 1/2000 | Grotz | 606/72 |
| 6,022,373 A | 2/2000 | Li | |
| 6,024,758 A | 2/2000 | Thal | |
| 6,045,574 A | 4/2000 | Thal | |
| 6,053,935 A | 4/2000 | Brenneman et al. | |
| 6,056,773 A | 5/2000 | Bonutti | |
| 6,068,648 A | 5/2000 | Cole et al. | |
| 6,149,669 A * | 11/2000 | Li | 606/232 |
| 6,156,039 A * | 12/2000 | Thal | 606/72 |
| 6,319,269 B1 * | 11/2001 | Li | 606/232 |

\* cited by examiner

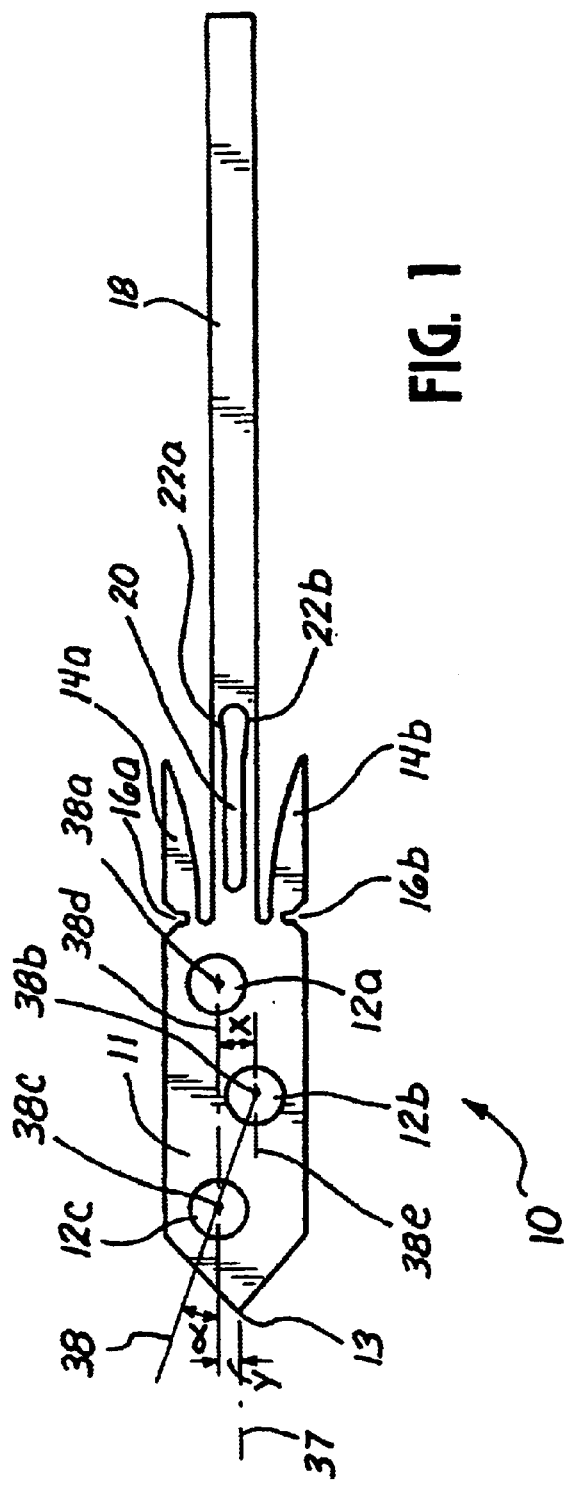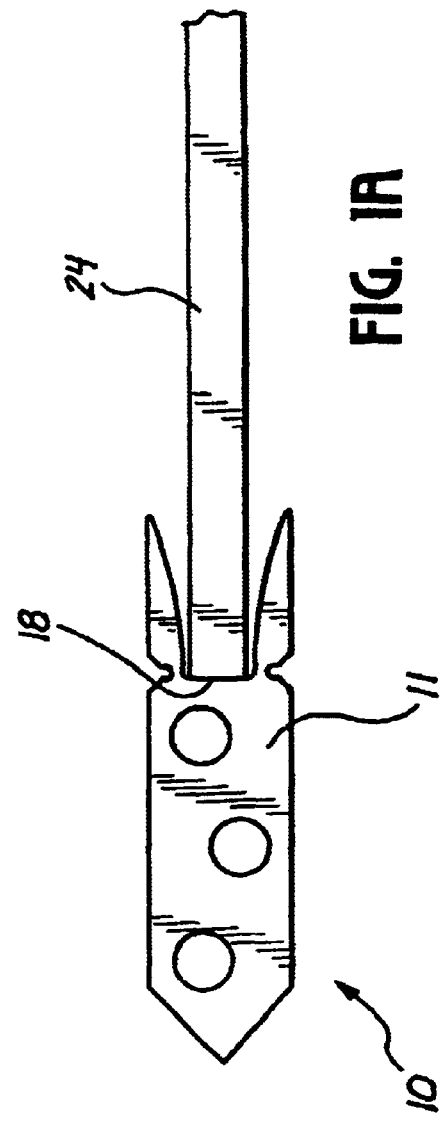

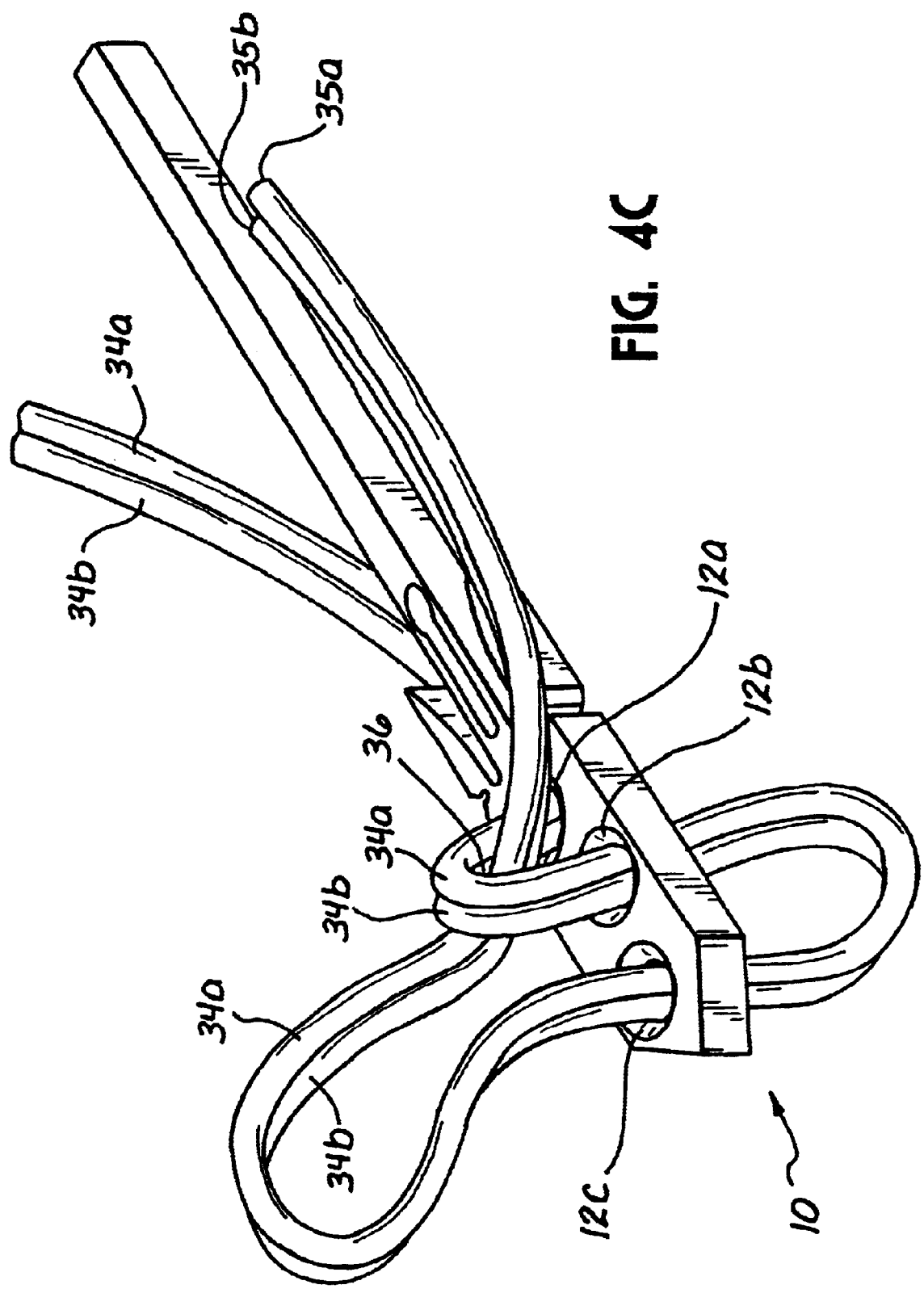

METHOD AND APPARATUS FOR ATTACHING CONNECTIVE TISSUES TO BONE USING A PERFORATED SUTURE ANCHORING DEVICE

BACKGROUND OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching the rotator cuff to the humeral head, in order to repair the rotator cuff.

It is an increasingly common problem for tendons and other soft, connective tissues to tear or to detach from associated bone. One such type of tear or detachment is a "rotator cuff" tear, wherein the supraspinatus tendon separates from the humerus, causing pain and loss of ability to elevate and externally rotate the arm. Complete separation can occur if the shoulder is subjected to gross trauma, but typically, the tear begins as a small lesion, especially in older patients.

To repair a torn rotator cuff, the typical course today is to do so surgically, through a large incision. This approach is presently taken in almost 99% of rotator cuff repair cases. There are two types of open surgical approaches for repair of the rotator cuff, one known as the "classic open" and the other as the "mini-open". The classic open approach requires a large incision and complete detachment of the deltoid muscle from the acromion to facilitate exposure. The cuff is debrided to ensure suture attachment to viable tissue and to create a reasonable edge approximation. In addition, the humeral head is abraded or notched at the proposed soft tissue to bone reattachment point, as healing is enhanced on a raw bone surface. A series of small diameter holes, referred to as "transosseous tunnels", are "punched" through the bone laterally from the abraded or notched surface to a point on the outside surface of the greater tuberosity, commonly a distance of 2 to 3 cm. Finally, the cuff is sutured and secured to the bone by pulling the suture ends through the transosseous tunnels and tying them together using the bone between two successive tunnels as a bridge, after which the deltoid muscle must be surgically reattached to the acromion. Because of this maneuver, the deltoid requires postoperative protection, thus retarding rehabilitation and possibly resulting in residual weakness. Complete rehabilitation takes approximately 9 to 12 months.

The mini-open technique, which represents the current growing trend and the majority of all surgical repair procedures, differs from the classic approach by gaining access through a smaller incision and splitting rather than detaching the deltoid. Additionally, this procedure is typically performed in conjunction with arthroscopic acromial decompression. Once the deltoid is split, it is retracted to expose the rotator cuff tear. As before, the cuff is debrided, the humeral head is abraded, and the so-called "transosseous tunnels", are "punched" through the bone or suture anchors are inserted. Following the suturing of the rotator cuff to the humeral head, the split deltoid is surgically repaired.

Although the above described surgical techniques are the current standard of care for rotator cuff repair, they are associated with a great deal of patient discomfort and a lengthy recovery time, ranging from at least four months to one year or more. It is the above described manipulation of the deltoid muscle together with the large skin incision that causes the majority of patient discomfort and an increased recovery time.

Less invasive arthroscopic techniques are beginning to be developed in an effort to address the shortcomings of open surgical repair. Working through small trocar portals that minimize disruption of the deltoid muscle, a few surgeons have been able to reattach the rotator cuff using various bone anchor and suture configurations. The rotator cuff is sutured intracorporeally and an anchor is driven into bone at a location appropriate for repair. Rather than thread the suture through transosseous tunnels which are difficult or impossible to create arthroscopically using current techniques, the repair is completed by tying the cuff down against bone using the anchor and suture. Early results of less invasive techniques are encouraging, with a substantial reduction in both patient recovery time and discomfort.

Unfortunately, the skill level required to facilitate an entirely arthroscopic repair of the rotator cuff is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of rotator cuff repair, this means that the knot bundle is left in the shoulder capsule where it is able to be felt by the patient postoperatively when the patient exercises the shoulder joint. So, knots tied arthroscopically are difficult to achieve, impossible to adjust, and are located in less than optimal areas of the shoulder. Suture tension is also impossible to measure and adjust once the knot has been fixed. Consequently, because of the technical difficulty of the procedure, presently less than 1% of all rotator cuff procedures are of the arthroscopic type, and are considered investigational in nature.

Another significant difficulty with current arthroscopic rotator cuff repair techniques are shortcomings related to currently available suture anchors. Suture eyelets in bone anchors available today, which like the eye of a needle are threaded with the thread or suture, are small in radius, and can cause the suture to fail at the eyelet when the anchor is placed under high tensile loads.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, airy and somewhat vascular interior of the bone). There is a clear demarcation between the cortical bone and cancellous bone, where the cortical bone presents a kind of hard shell over the less dense cancellous bone. The aspect ratio of the anchor is such that it typically has a longer axis and a shorter axis and usually is pre-threaded with a suture. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment in to the cancellous bone, the anchor is rotated 90° so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pull-out. These anchors still suffer from the aforementioned problem of eyelet design that stresses the sutures.

Still other prior art approaches have attempted to use a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, ostensibly locking the device into the bone.

Other methods of securing soft tissue to bone are known in the prior art, but are not presently considered to be feasible for shoulder repair procedures, because of physicians's reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

As previously discussed, any of the anchor points for sutures mentioned above require that a length of suture be passed through an eyelet fashioned in the anchor and then looped through the soft tissues and tied down to complete the securement. Much skill is required, however, to both place the sutures in the soft tissues, and to tie knots while working through a trocar under endoscopic visualization.

What is needed, therefore, is a new approach for repairing the rotator cuff or fixing other soft tissues to bone, wherein suture tension can be adjusted and possibly measured, the suture resides completely below the cortical bone surface, there is no requirement for the surgeon to tie a knot to attach the suture to the bone anchor, and wherein the procedure associated with the new approach is better for the patient, saves time, is uncomplicated to use, and easily taught to practitioners having skill in the art.

SUMMARY OF THE INVENTION

The present invention solves the problems outlined above by providing innovative bone anchor and connective techniques which permit a suture attachment which lies beneath the cortical bone surface. In the present state of the art, the sutures which are passed through the tissues to be attached to bone typically are threaded through a small eyelet incorporated into the head of the anchor and then secured by tying knots in the sutures. Endoscopic knot tying is an arduous and technically demanding task. Therefore, the present invention discloses devices and methods for securing sutures to a bone anchor without the requirement of knot tying.

In one aspect of the invention, there is provided a bone anchor device for attaching connective tissue to bone, which comprises an anchor body, a plurality of suture retaining apertures disposed in the anchor body, and deployable structure for securing the anchor body in bone. The term "plurality of suture retaining apertures" means at least two, but three suture retaining apertures are employed in the presently preferred embodiment.

A longitudinal axis is disposed along a center of the anchor body, wherein the plurality of suture retaining apertures are spaced axially relative to one another. Additionally, in preferred embodiments, at least two of the plurality of suture retaining apertures are transversely offset from one another relative to the longitudinal axis. Most preferably, a first of the at least two of the plurality of suture retaining apertures is disposed on one side of the longitudinal axis and a second of the at least two of the plurality of suture retaining apertures is disposed on the other side of the longitudinal axis. In other words, the two apertures are in a staggered orientation along the axis, with one on one side of the axis, and the other on the other side of the axis. The advantage of this configuration is that, as the suturing material is threaded through the axially spaced suture retaining apertures, because the apertures are offset from one another transversely, relative to the axis, the suturing material is wrapped in an angular orientation relative to the axis. This permits the suturing material to be wrapped over itself as it is threaded through the suture retaining apertures, in an "over and back" fashion, as will be described more fully hereinbelow.

In a preferred embodiment, the aforementioned deployable structure comprises a pair of deployable flaps. The anchor body comprises a substantially planar surface in which the plurality of suture retaining apertures are disposed. In its presently preferred embodiment, the anchor body comprises opposing substantially flat surfaces, wherein the plurality of suture retaining apertures extend through the entire anchor body. A stem extends proximally from a proximal end of the anchor body. At least a portion of a longitudinal slit is disposed in the stem.

In another aspect of the invention, a bone anchor device is provided for attaching connective tissue to bone. The bone anchor device comprises an anchor body having opposing substantially flat surfaces, deployable structure on a proximal end of the anchor body for securing the anchor body in bone; and a suture retaining aperture extending through the anchor body flat surfaces. The suture retaining aperture is disposed distally of the deployable structure.

In yet another aspect of the invention, there is provided a bone anchor device for attaching connective tissue to bone, which comprises an anchor body having a distal end and a proximal end. A stem extends proximally from the proximal end of the anchor body. A deployable flap is disposed on the proximal end of the anchor body, and a notch on the anchor body is disposed at a location joining the anchor body and the deployable flap. The notch is adapted to cause the deployable flap to deploy outwardly when force is applied to a proximal end of the deployable flap by an actuator which moves distally relative to the deployable flap.

In another aspect of the invention, there is provided a bone anchor device for attaching connective tissue to bone. This inventive device comprises an anchor body having a distal end and a proximal end and a stem extending proximally from the proximal end of the anchor body. A deployable flap is disposed on the proximal end of the anchor body. The inventive device further comprises a slit, at least a portion of which is disposed in the stem.

In still another aspect of the invention, there is provided a bone anchor device for attaching connective tissue to bone. The inventive device comprises an anchor body having two opposing surfaces, and a suture retaining aperture disposed in the anchor body and extending through both of the opposing surfaces. A length of suturing material extends through the suture retaining aperture, wherein the length of suturing material is looped about the anchor body and contacts substantial portions of both of the two opposing surfaces. Advantageously, in order to fully lock the suturing material in place on the anchor body, a first portion of the length of suturing material is looped over a second portion of the length of suturing material, the second portion of which lies in contacting engagement with one of the opposing surfaces of the anchor body.

Preferably, a second suture retaining aperture is disposed in the anchor body in axially spaced relation to the suture retaining aperture, wherein the length of suture retaining material is looped through both of the suture retaining apertures.

In yet another aspect of the invention, there is disclosed a method for securing connective tissue to bone. This inventive method comprises a step of securing a first end of a length of suture to a portion of soft tissue to be attached to a portion of bone. A second end of the length of suture is threaded sequentially through a plurality of suture retaining apertures in a body of a bone anchor device so that the length of suture is securely fastened to the bone anchor body. The bone anchor body is placed in a blind hole disposed in the aforementioned portion of bone. Then, structure on the bone anchor body is deployed in an outward direction to secure the bone anchor body in the blind hole.

The invention, together with additional features and advantages thereof, may best be understood by reference to the following description taken in conjunction with the accompanying illustrative drawing.

BRIEF DESCRIPTION OF THE DRAWINGS

FIG. 1 is a plan view of a presently preferred embodiment of the inventive bone anchor device; FIG. 1A is a plan view of the inventive bone anchor device illustrated in FIG. 1, wherein the stem of the device has been inserted into a hollow casing;

FIGS. 4A–4E are perspective views of the inventive bone anchor device shown in FIGS. 1–3C, illustrating in sequence a preferred method for threading the device with suturing material;

DESCRIPTION OF THE PREFERRED EMBODIMENT

Figure 2:
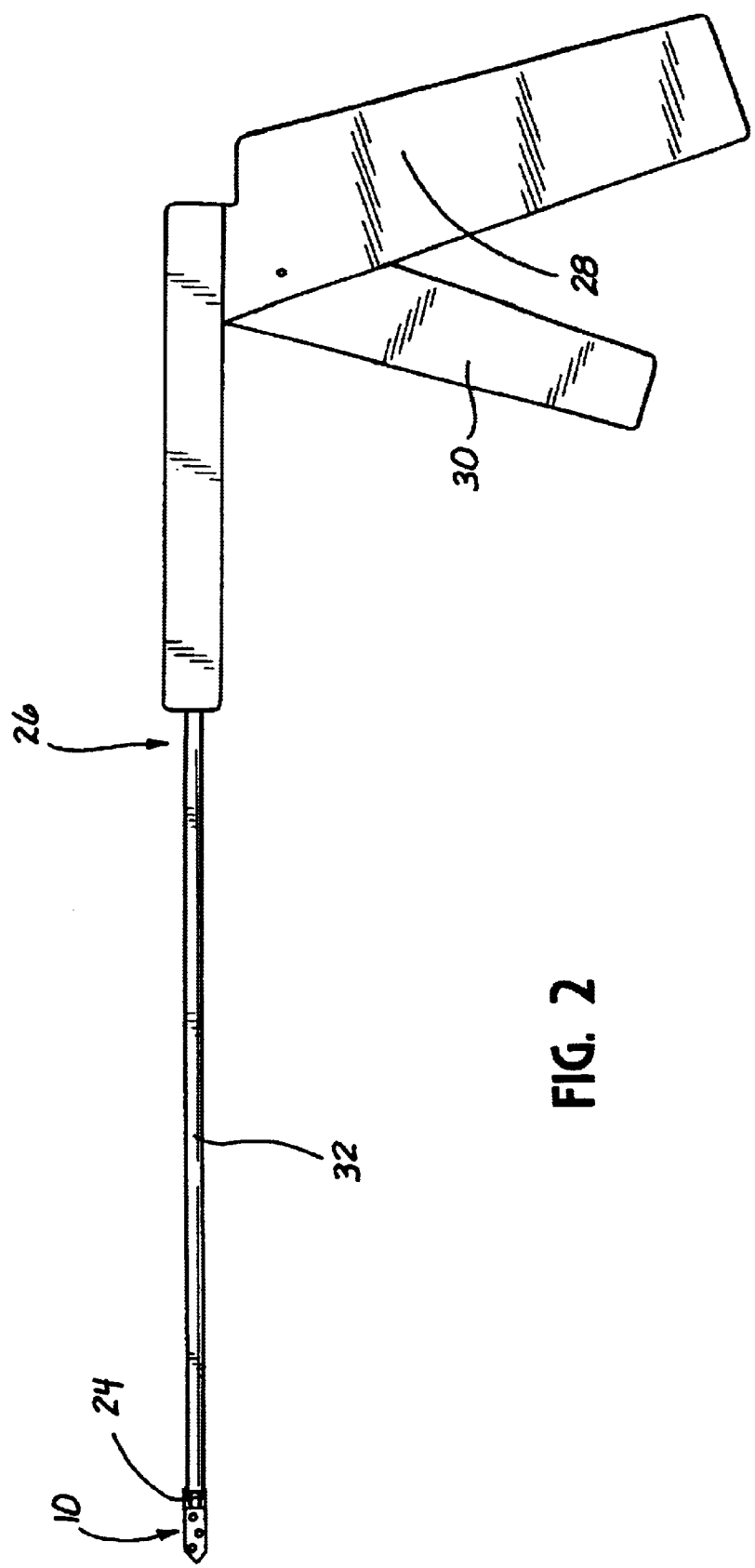
FIG. 2 is a plan schematic view illustrating a preferred deployment system for a bone anchoring device of the type shown in FIGS. 1 and 1A.

Referring now more particularly to the drawings, there is shown in FIG. 1 a bone anchor 10 in its undeployed state. The distal end of the bone anchor 10 is comprised of a substantially flat body 11 which preferably has three eyelet holes or suture retaining apertures 12a, 12b, and 12c, and which comes to a point 13 at a distal end where it is to be inserted into the bone. Two deployable flaps 14a, 14b are defined by two notches 16a,b which allow for deployment of the flaps, and are disposed at a point where the flaps 14a, 14b are attached to the flat body 11. To a proximal end of the bone anchor is joined a relatively narrow stem 18. A slit 20 is disposed at least partially on the stem 18 and partially on the flat body 11, although in presently preferred embodiments, the slit 20 is disposed entirely on the stem 18, as shown in FIG. 1. Weak links 22a, 22b are formed on either side of the slit 2.

As shown in FIG. 1a, the proximal end of the stem 18 of the bone anchor 10 is preferably inserted into a hollow casing 24, which in turn has been attached to the stem 18 utilizing methods well known in the art such as crimping, welding or the like, in order to secure the bone anchor 10 to the casing 24. The casing 24 is intended to provide an easy means for insertion of the bone anchor apparatus 10 into a deployment device for deploying the bone anchor as shall be more fully described and illustrated hereinbelow. It is to be understood, of course, that the flat form of the bone anchor 10 and the shape of the casing 24 are used herein for informational purposes as to possible methods of fabrication only, and are not to be deemed limiting.

Referring now to FIG. 2 there is illustrated a deployment device 26 which may, for example, be used to deploy the bone anchor 10. This representative deployment device 26 includes a handle 28, a trigger 30, and a hollow barrel 32 into which the casing 24 on the proximal end of the bone anchor 10 has been inserted for deployment. Although many methods of deployment may be utilized, in the deployment device 26 herein illustrated, the proximal end of the casing 24 is coupled to the trigger mechanism 30 through the barrel 32 of such deployment device 26. When the trigger mechanism 30 is activated, the proximal end of the casing 24 is pulled into the hollow barrel 32 until the distal end of the hollow barrel 32 comes into contact with the flaps 14a, 14b on the bone anchor 10, thus applying a distally-directed force thereon and thereby deploying such flaps 14a, 14b, as shall be shown and described below.

Figure 3A:
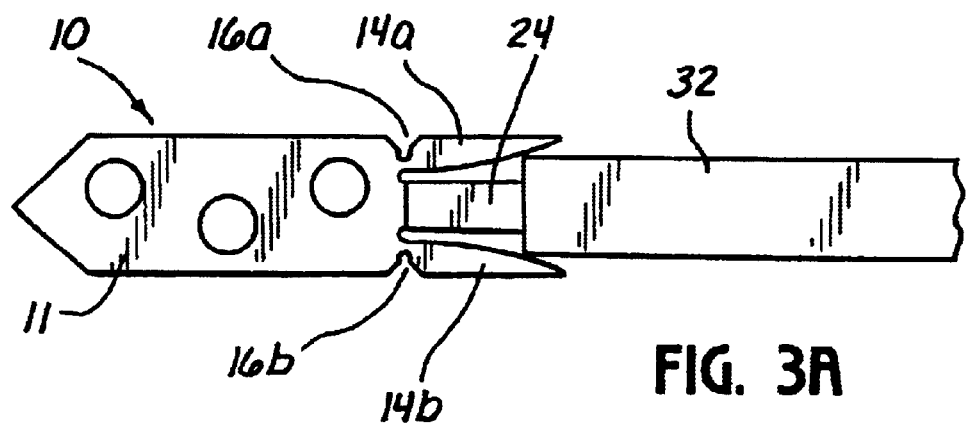
FIGS. 3A–3C are plan views similar to those of FIGS. 1 and 1A, illustrating in sequence a preferred method for deploying the bone anchor device of the present invention.
Figure 3B:
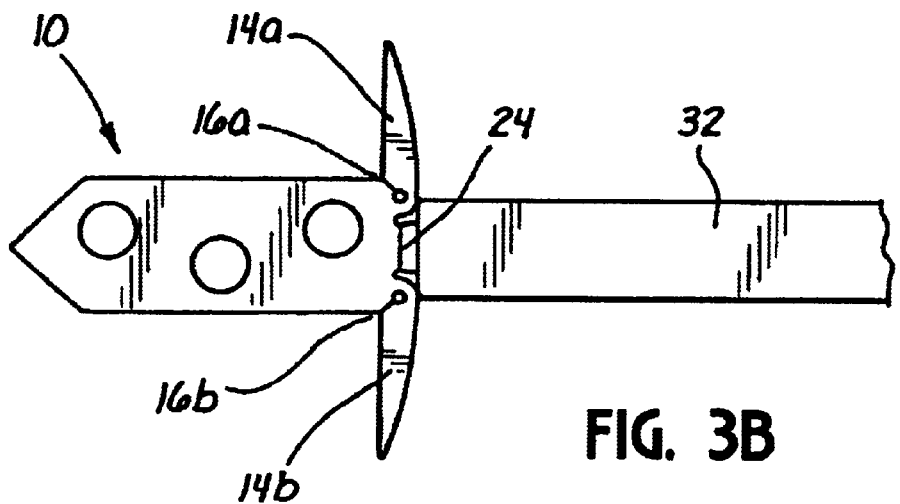
Figure 3C:
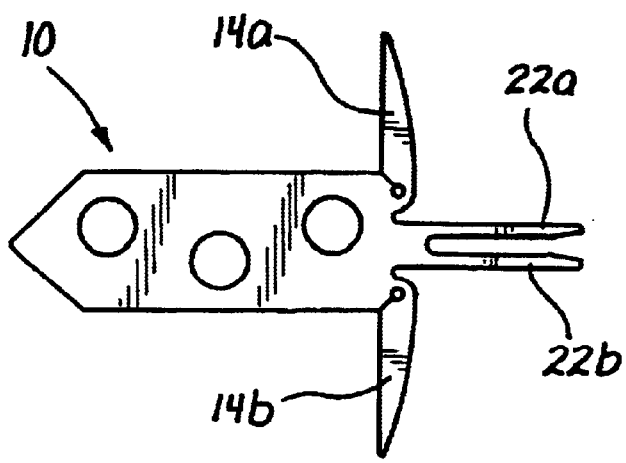

Referring now to FIG. 3A, the casing 24 that has been crimped or otherwise attached to the bone anchor 10 is shown inserted into the barrel 32 of the deployment device 26 (FIG. 2) before deployment of the anchor flaps 14a, 14b. As seen in FIG. 3B, the barrel 32 is driven in a distal direction (or, preferably, the casing 24 is drawn into the barrel 32), which causes the distal end of the barrel 32 to come into contact with flaps 14a, 14b. By continuing to move the barrel 32 distally, relative to the flaps 14a, 14b, once the aforementioned contact has been made, force will be applied against the base of each flap, causing each flap to bend outwardly at its respective notch 16a, 16b as shown in FIG. 3B. The result is that the flaps 14a, 14b are deployed outwardly from the body of the bone anchor 10.

Figure 4A:
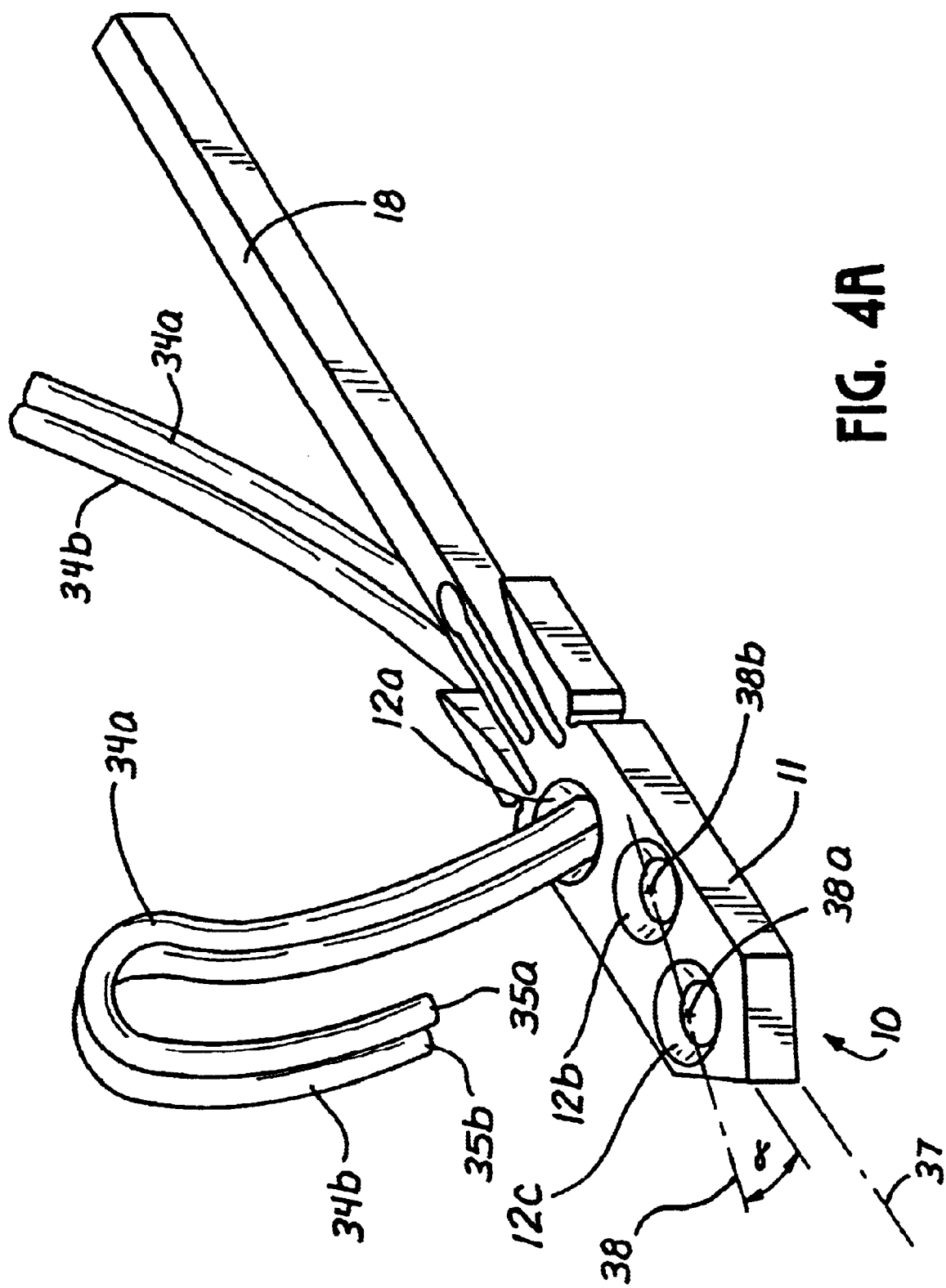
Figure 4B:
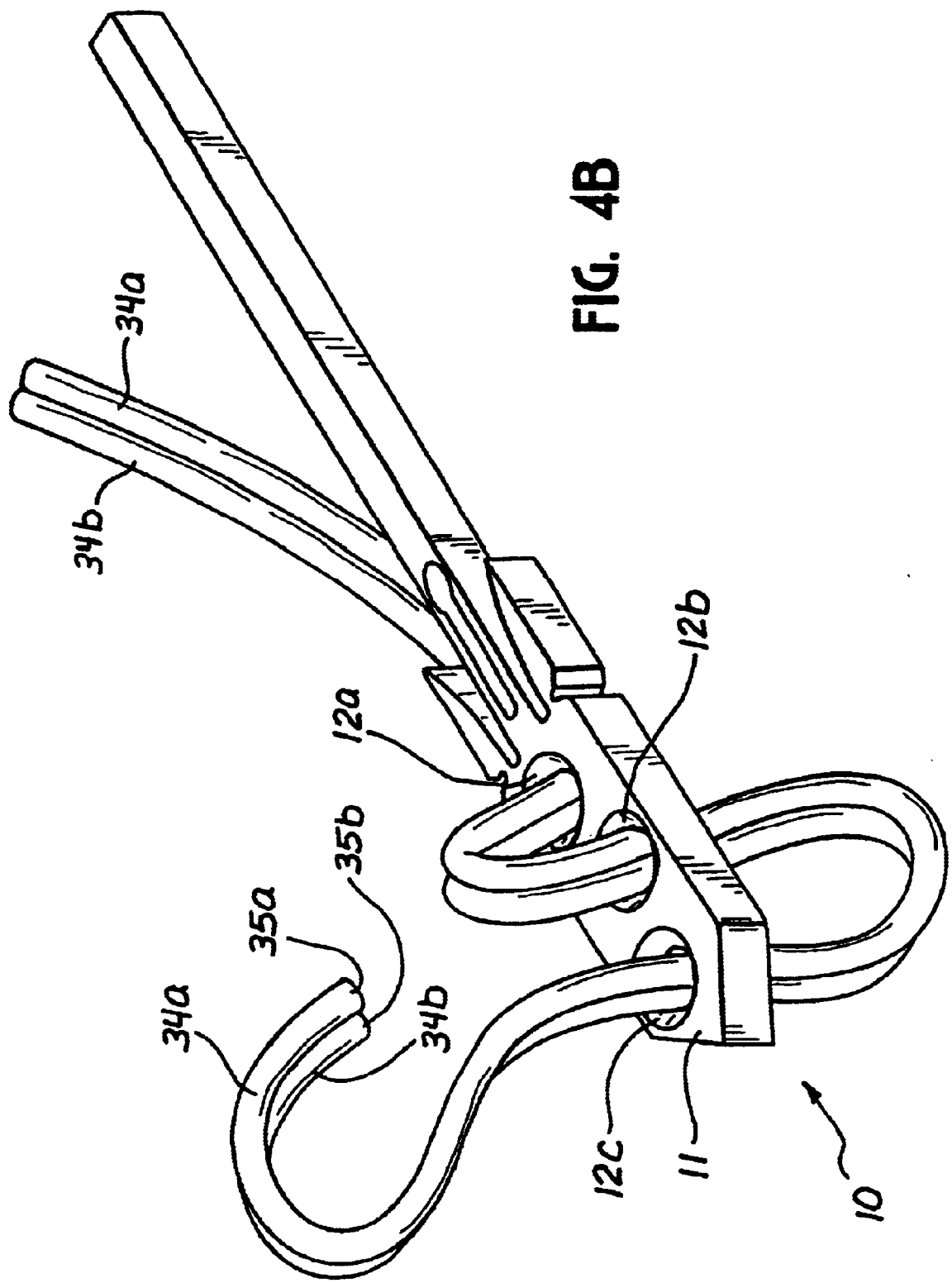

As the deployment force exerted by the barrel 32 is taken directly on the face of the flaps 14a, 14b, as noted supra, the notches 16a, 16b close and limit the X bending of the flaps 14a, 14b, and the load on the weak links 22a, 22b on opposing sides of the slit 20 begins to increase as a result of the imposition of a tensile force on the proximal end of the bone anchor after the distal end thereof has been anchored into the bone. In other words, because the anchor body 11 is fixed in the bone, and cannot move responsive to the applied tensile force, the reactive force applied by the anchor body on the stem 18 causes the weak links 22a, 22b to fracture, thereby separating the casing 24 em and the broken stem 18 from the bone anchor 10, leaving the bone anchor 10 anchored into the bone structure. Referring to FIGS. 4a–4e, it may be seen how suture may be attached to the bone anchor apparatus 10, in accordance with one preferred method, prior to its deployment into the bone structure. As illustrated in FIG. 4a, adjacent lengths of suture 34a, 34b have two corresponding free ends 35a, 35b, respectively, which have already been disposed through a tendon or portion of soft tissue (not shown), and then are passed from the underside of the bone anchor 10 in its undeployed state through the eyelet hole 12a. In actuality, as will be explained in more detail hereinbelow, the two suture lengths 34a, 34b represent the free ends of a length of suture which has been looped through a portion of soft tissue in the form of a mattress stitch. In FIG. 4b, the suture lengths 34a, 34b are then threaded from the top side of the bone anchor body 11 through the eyelet 12b to the underside of the anchor body 11, and then back up to the top side thereof through the eyelet hole 12c. In FIG. 4c the loose or free ends 35a, 35b of the suture lengths 34a, 34b, respectively, are passed, as illustrated, through a loop 36, which is formed by a portion of the lengths of suture 34a, 34b, on the top side of the bone anchor between eyelet holes 12a,b.

An important feature of the present invention concerns the placement of the suture retaining apertures or eyelet holes 12a, 12b, and 12c. As illustrated in FIG. 4a, the bone anchor 10 of the present invention has a longitudinal axis 37 extending along its axial center. In the illustrated preferred embodiment, each of the suture retaining apertures 12a, 12b, and 11c are axially spaced and are offset from the longitudinal axis in a transverse direction (meaning the direction orthogonal to the axis). This offset can be measured by measuring the distance from the longitudinal axis 37 to a center of the suture retaining aperture. More preferably, successive suture retaining apertures (i.e. 12a and 12b or 12b and 12c) are offset in a "staggered" fashion, meaning they are offset from the longitudinal axis in opposed transverse directions. The purpose for this offset is to ensure that the suturing material, as it is threaded through the apertures in a distal direction (FIG. 4b), and then returned in a proximal direction beneath the loop 36 (FIG. 4c), lies at an angle relative to the longitudinal axis 37. Without this angled orientation, the suture loop lock feature of the invention would not be as easy to achieve, nor as effective.

In one presently preferred embodiment, as illustrated in FIGS. 1 and 4a, an angle a between a line 38 which lies between a center point 38b of aperture 12b and a center point 38c of aperture 12c, and the longitudinal axis 37 preferably falls within a range of approximately 10–30 degrees, and is most preferably about 18–25 degrees. In the preferred embodiment shown, the angle a is between 19 and 20 degrees. The inventor has found that if the angle a is too great, improper suture locking may occur, and, conversely, there may be an inadequate ability to adjust the suture once it has been threaded about the anchor body.

Additionally, as shown in FIG. 1, in the presently preferred embodiment, the distance x between a centerline 38d running between center points 38a and 38c of apertures 12a and 12c and a centerline 38e running through center point 38b of aperture 12b is approximately 0.035 inches. A distance y from the axis 37 to the centerline 38d is 0.0175 inches in the same preferred embodiment, which, of course, means that the aperture 12b is equally offset 0.0175 inches from the axis 37 in the opposing transverse direction. Of course, these specific distances are merely exemplary, and are not required for successful implementation of the inventive concept. For example, they may be scaled to differently sized instruments. It is also possible to implement the invention without utilizing suture retaining apertures which are equally spaced from the longitudinal axis 37, or which are offset from the axis 37 at all. Such an embodiment is shown, for example, in FIG. 7, which will be discussed hereinbelow.

Figure 4D:
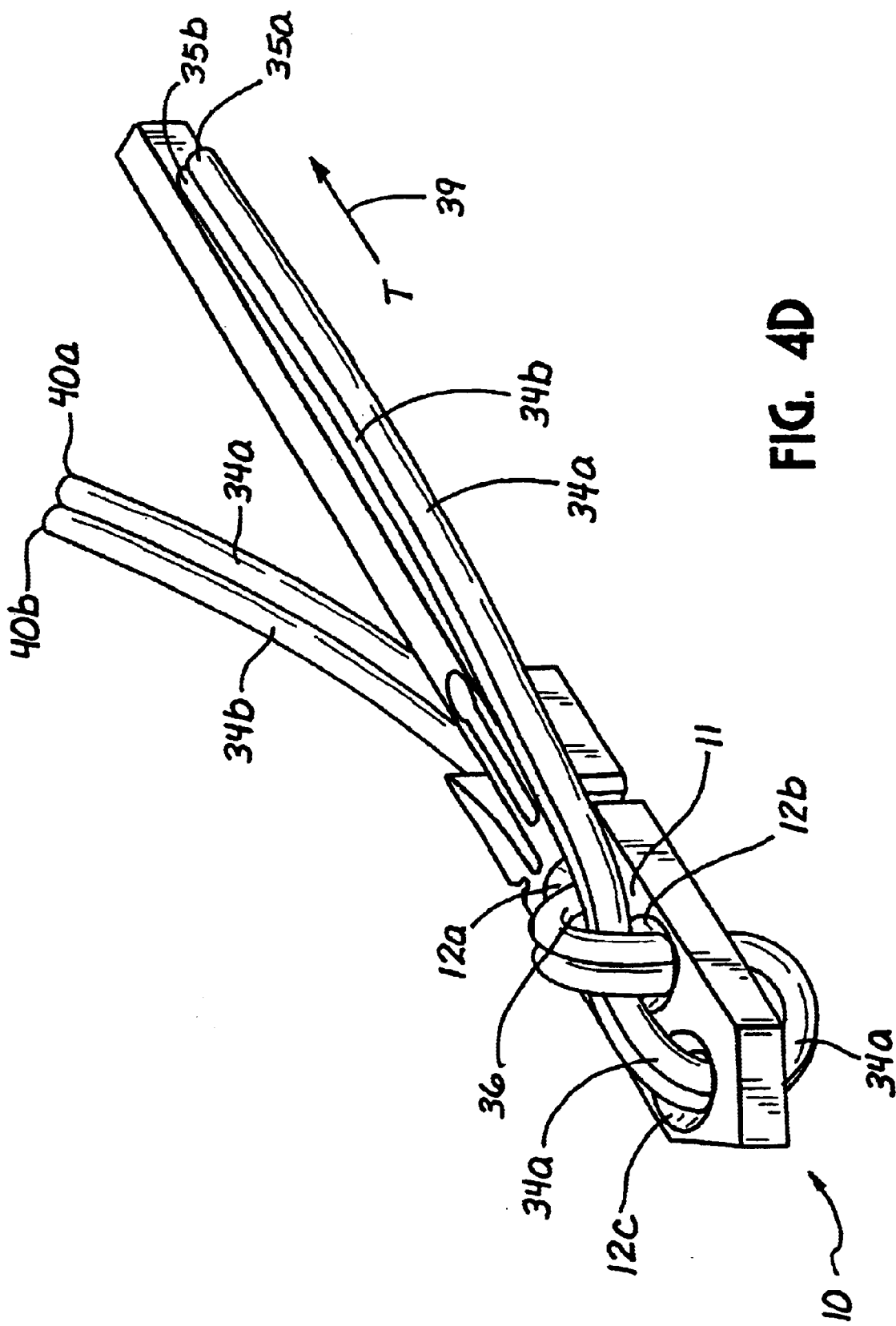
Figure 4E:
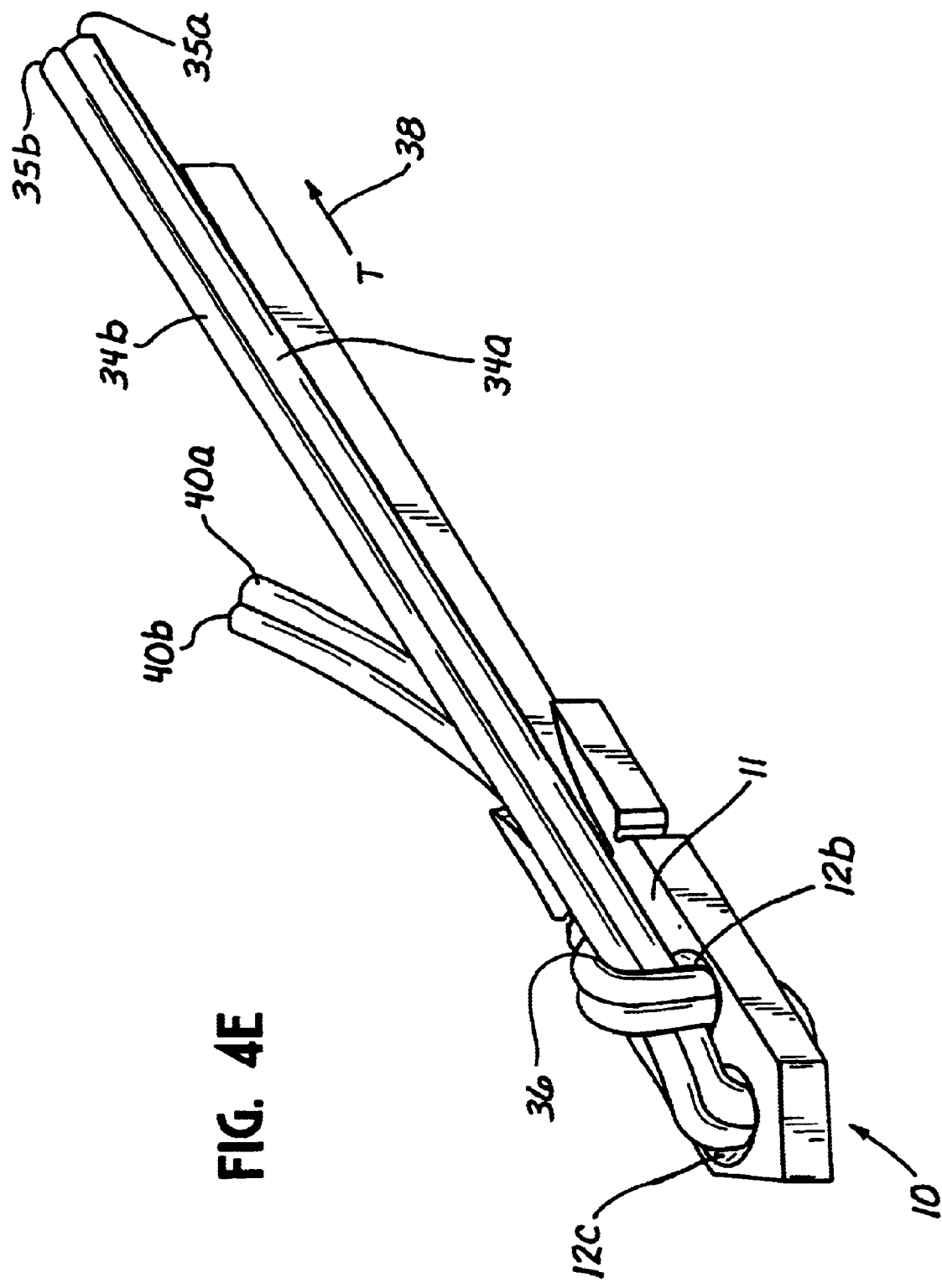

In FIGS. 4d and 4e, the free ends 35a, 35b of the suture lengths 34a, 34b, respectively, are drawn snugly by creating a tension as represented by the letter T in he direction of the arrow 39 in order to eliminate any slack at the fixation point of he suture lengths 34a, 34b to the bone anchor 10 as well as to create tension in the suture lengths 34a, 34b that is disposed, in turn, through the tendon or soft tissue to be attached to bone by the bound ends 40a, 40b, respectively, of the suture lengths 34a, 34b. It is to be understood that it is the combination of the tension in the suture lengths 34a, 34b and the passing of the suture lengths 34a, 34b beneath the loop 36 that defines the inventive locking aspect of the invention. It may be seen that as the tension in the suture lengths 34a, 34b is increased on the free ends 35a, 35b, respectively, the suture lengths 34a, 34b are drawn through the eyelets 12a, 12b, 12c and through the loop 36, creating greater and greater tension on the bound legs 40a, 40b, which by direct contact through the suture loop 36, locks the free suture lengths 34a, 34b against the flat body 11 of the bone anchor 10.

It is to be understood, of course, that while we have been talking about a preferred case of two free lengths 34a, 34b of suture which extend from two bound ends 40a, 40b thereof, wherein the bound ends are actually the two opposing ends of a loop of suture extending through a portion of soft tissue in the form of a mattress stitch, this invention is equally well adapted to the use of a single length of suture, or a plurality of lengths of suture greater than two, if desired.

Referring now to FIGS. 5a–5i, it can be seen more particularly how the inventive apparatus may be utilized, in one preferred procedure, as a bone anchor for the attachment of soft tissues to bone. It should be noted, in this respect, that those elements which are common to elements shown in FIGS. 1–4e are designated by common reference numerals. Now, in FIG. 5a there is shown a cross-sectional view of a human shoulder on the left side of the body as seen from the front of the body and which illustrates a rotator cuff tendon 46 which is disposed across a humeral head 48. It is to be understood that, in this illustration, the rotator cuff tendon is detached from the humeral head 48 at the interface 50 between the two. This is the problem which is to be corrected by the inventive procedure. The humeral head 48 is comprised of an outer surface of cortical bone 52 and inner cancellous bone 54. To allow for arthroscopic access, a trocar 56 has been inserted into the shoulder in proximity to the area where the rotator cuff tendon 46 is to be reattached to the humeral head 48, and a hole 58 has been made, preferably by drilling or punching, in the desired location through the cortical bone 52 and into the cancellous bone 54. This illustration is intended only to provide a simple structural overview of the physiological elements involved in a typical situation where it is to be desired that soft tissue such as a rotator cuff tendon 46 be reattached to a humeral head 48. However, it should be clear that the inventive procedure may be used in other areas of the body where soft tissue is to be reattached to bone.

Alternate rotator cuff repair procedures are also discussed in U.S. patent application Ser. No. 09/475,495, filed on Dec. 30, 1999, and entitled *Method and Apparatus for Attaching Connective Tissues to Bone Using a Knotless Suture Anchoring Device*, which is herein expressly incorporated by reference.

Figure 5A:
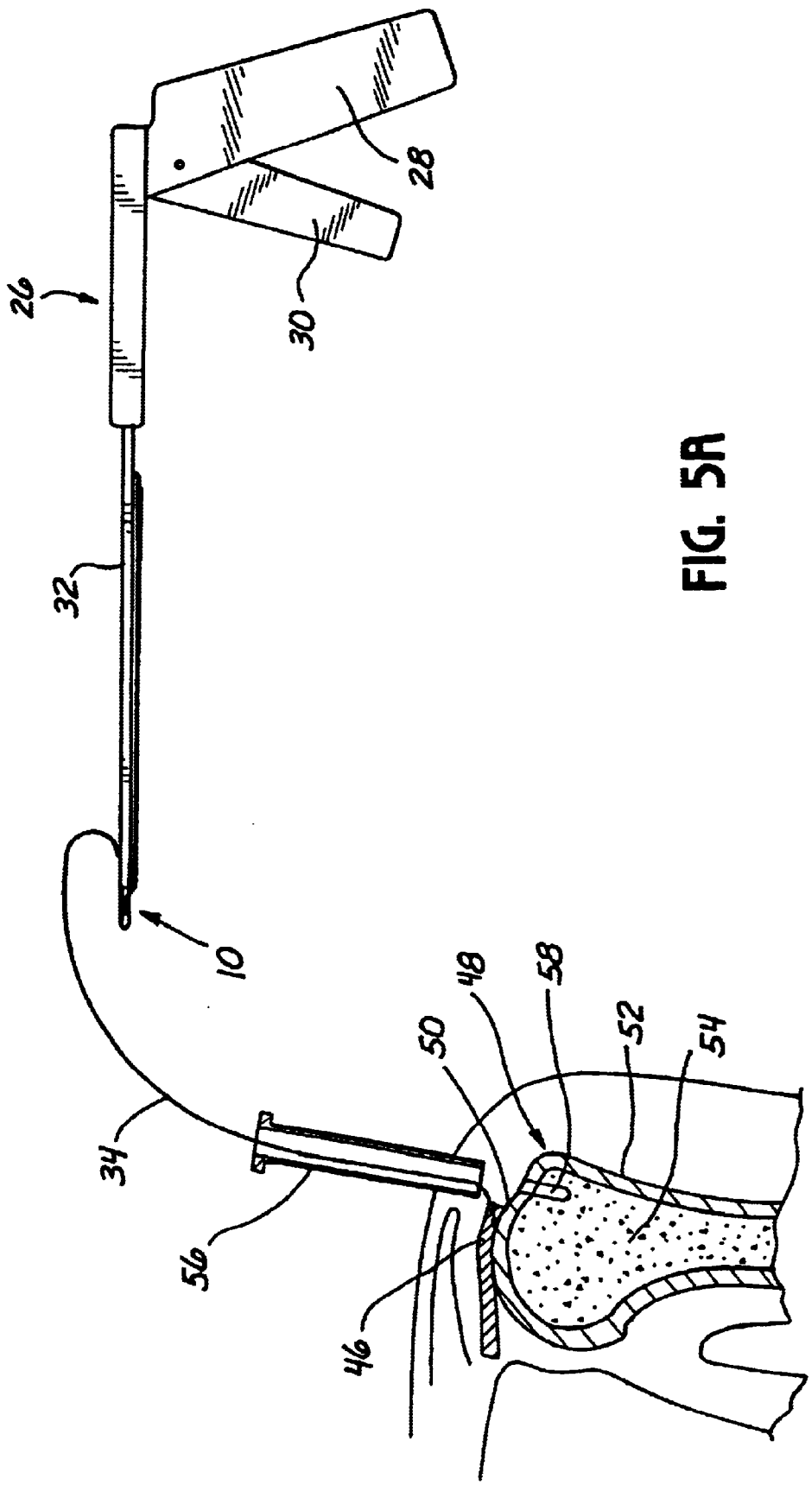
FIGS. 5A–5I are diagrammatic plan views, in sequence, illustrating one preferred method of using the inventive bone anchor device in the attachment of soft tissue to bone, in this case, the repair of a torn rotator cuff.

Referring still to FIG. 5a it can be seen that a length of suture 34 has been passed through the tendon 46 with the loose or free ends of the suture passing through the trocar and out of the shoulder. This step of suturing the tendon 46 is beyond the scope of the present application, but any known technique may be utilized. The present invention is particularly suited, however, to the use of a suturing instrument, as described in U.S. patent application Ser. No. 09/668,055, entitled *Linear Suturing Apparatus & Methods*, filed on Sep. 21, 2000, which is commonly assigned with the present application and is herein expressly incorporated by reference. This type of suturing instrument will produce a "mattress stitch" through the tendon 46, which is a preferred stitch for most practitioners. The free ends of the suture 34 have been threaded through the bone anchor 10 as previously described in connection with FIGS. 4a–c, above, and the proximal end of the bone anchor 10 has been inserted into the barrel 32 of the deployment device 26 as also previously described in connection with FIG. 2, above.

Figure 5B:
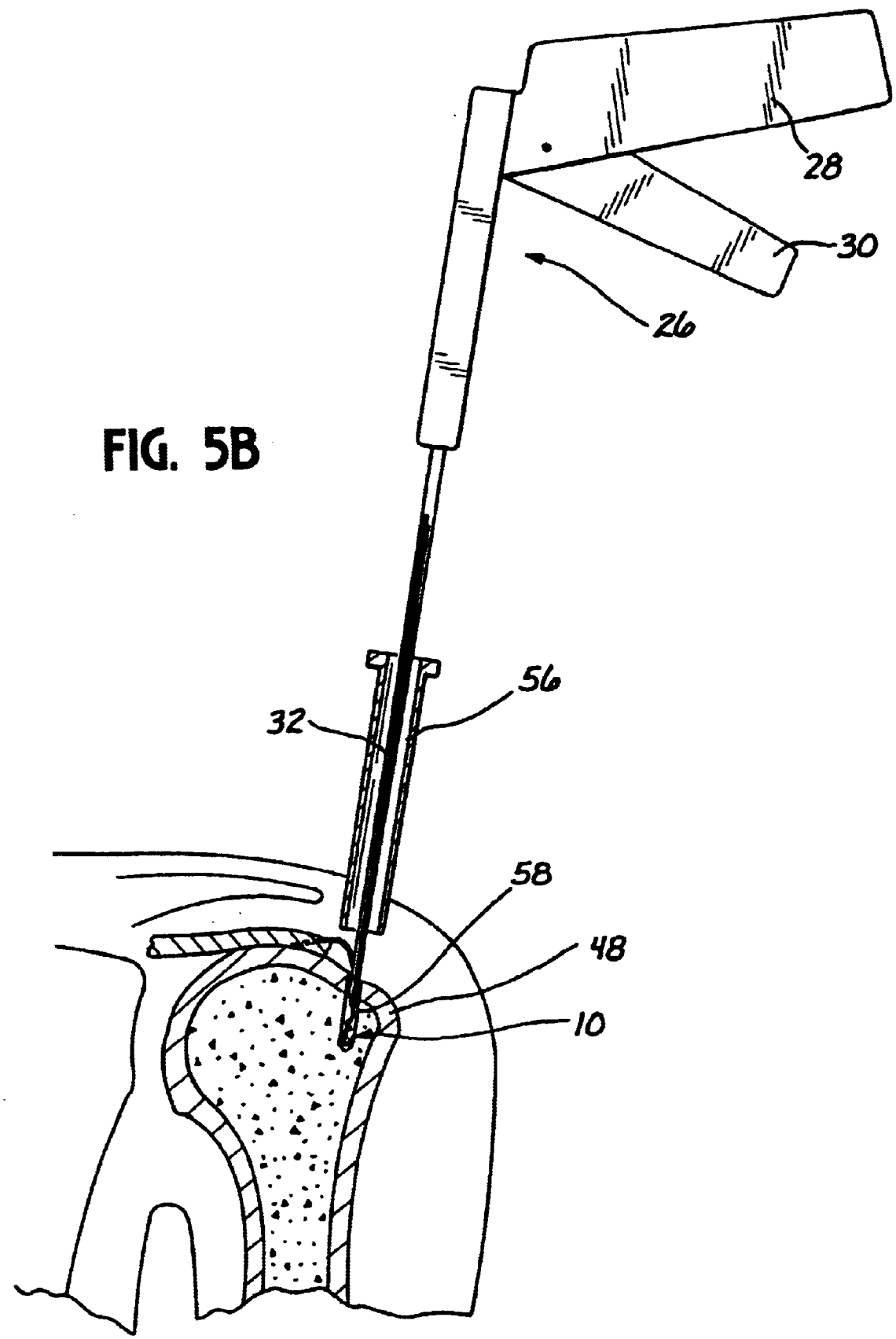

FIG. 5b illustrates in enlarged detail how the bone anchor 10 is inserted through the trocar 56 by means of the barrel 32 of the deployment device 26 and into the hole 58 which has been made in the humeral head 48.

Figure 5C:
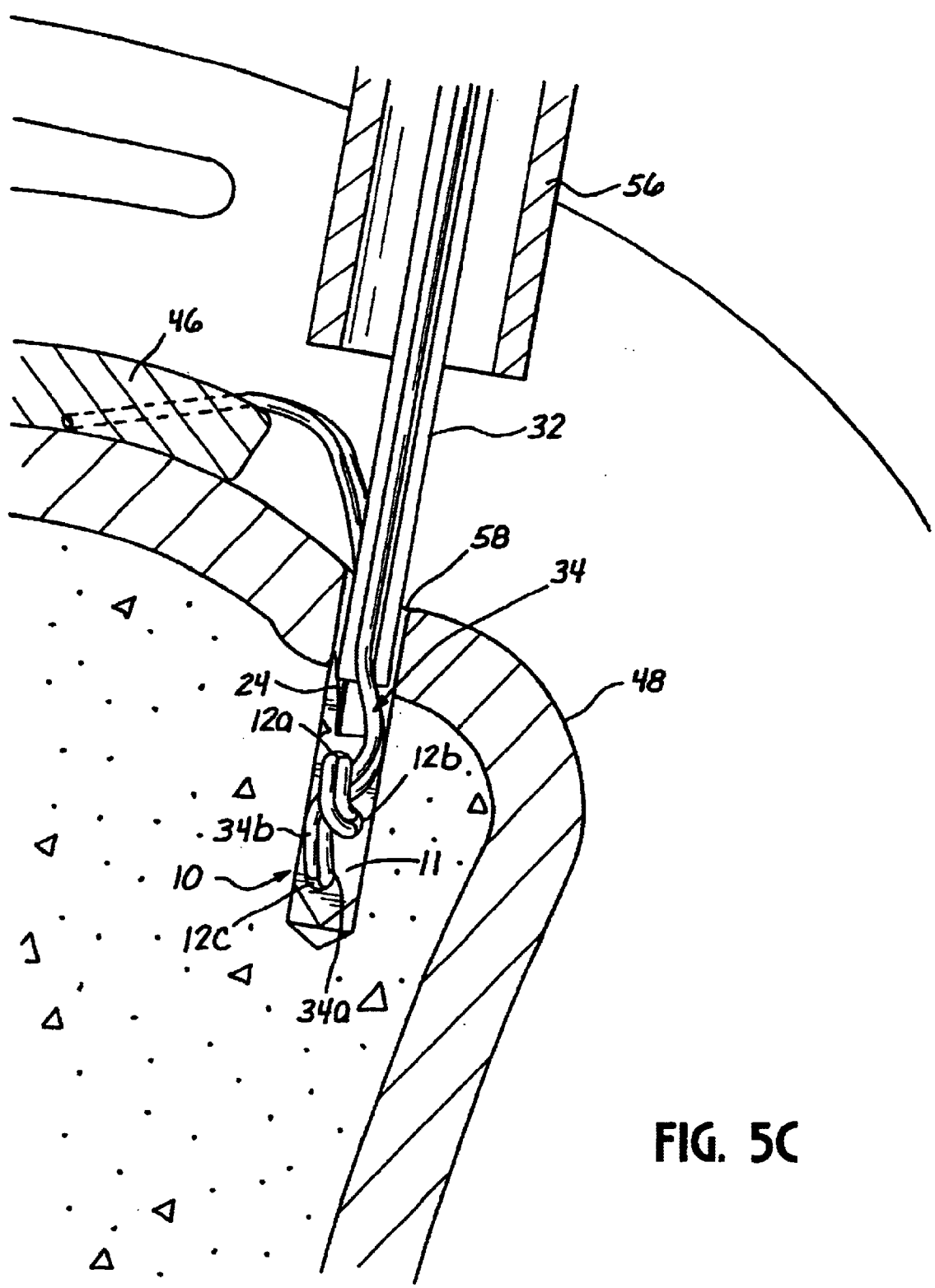

In FIG. 5c, a further enlarged view of the same general illustration is provided, detailing the distal end of the instrument and the procedural site. It can be seen in this view that each suture length or free leg 34a, 34b of the suture 34 has been drawn tight against the bone anchor 10 by applying continual tension to the free ends 35a, 35b(not shown —they extend proximally out through the barrel 32) of the suture 34 as the bone anchor is inserted through the trocar 56 and into the hole 58 in The humeral head 48.

Figure 5D:
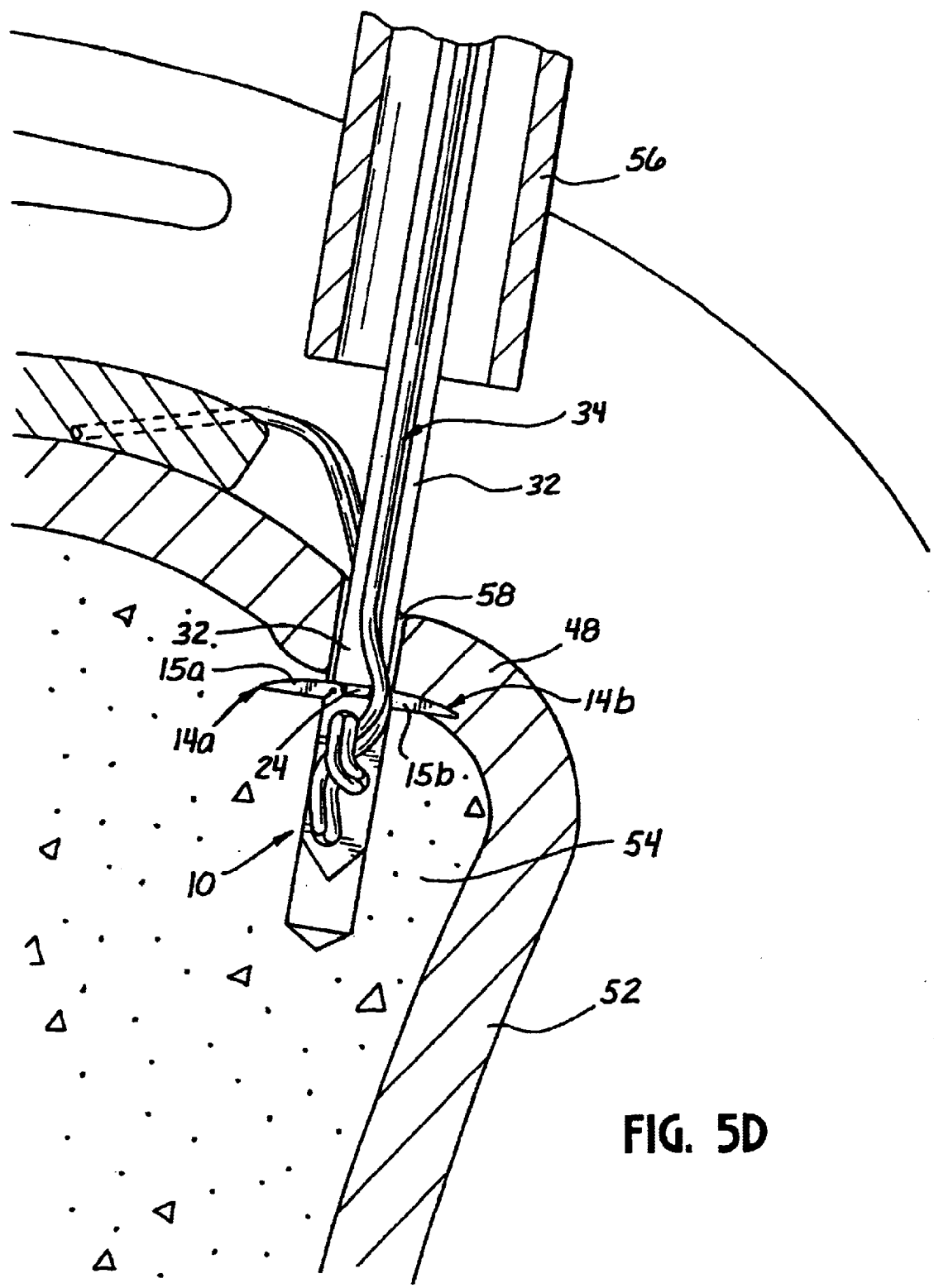

The bone anchor of FIG. 5c is still in its undeployed state. In FIG. 5d the bone anchor device has been deployed by activating the trigger mechanism of the deployment device 26 as illustrated in FIG. 2 and described above. Activation of such triggering mechanism causes the casing 24 which is attached to the proximal end of the bone anchor 10 to be pulled proximally into the barrel 32 of the deployment device. As the bone anchor is pulled into the barrel 32 the flaps 14a, 14b of the bone anchor impact against the end of the barrel 32, deploying such flaps outward from the bone anchor 10 in proximity to the interface of the cortical bone 52 and the cancellous bone 54. The flaps 14a, 14b bear against the inside of the cortical bone 52, thereby preventing the bone anchor from being retracted proximally out of the hole 58 in the cortical bone 52. Any rotational moment is also resisted by the flaps 14a, 14b, and more specifically by the edges 15a, 15b of the flaps 14a, 14b.

Figure 5E:
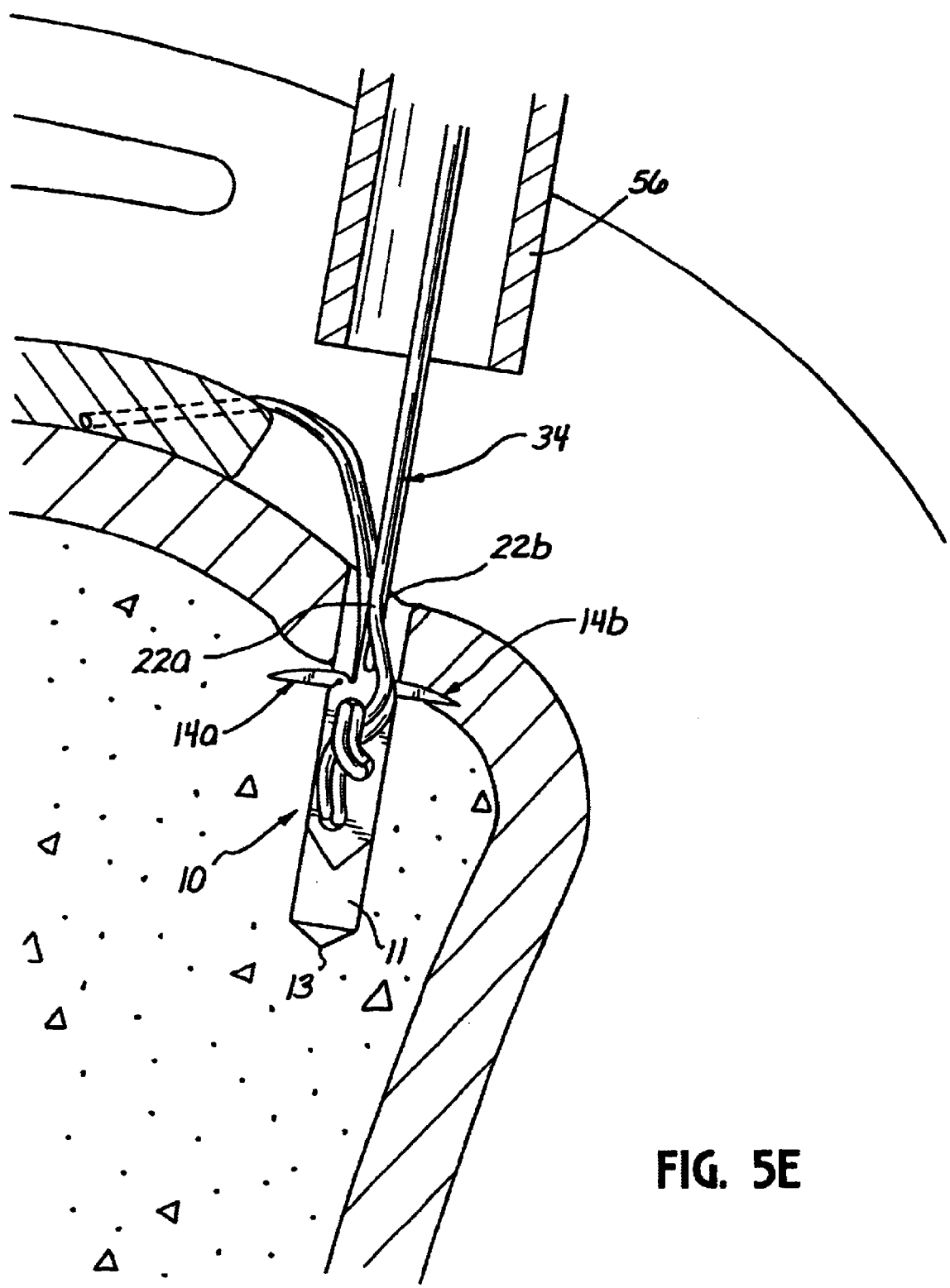

In FIG. 5e the barrel 32 of the deployment device has been removed from the trocar 56 by withdrawing it proximally through such trocar. As previously described in connection with FIGS. 3a through 3c, the tension imposed on the casing which is attached to the bone anchor stem as illustrated in FIG. 1a causes the weak links 22a, 22b to break, thereby separating the casing 24 from the bone anchor 10 and allowing the casing to be removed and discarded, and leaving the bone anchor 10 permanently disposed within the cancellous bone of the shoulder.

Figure 5F:
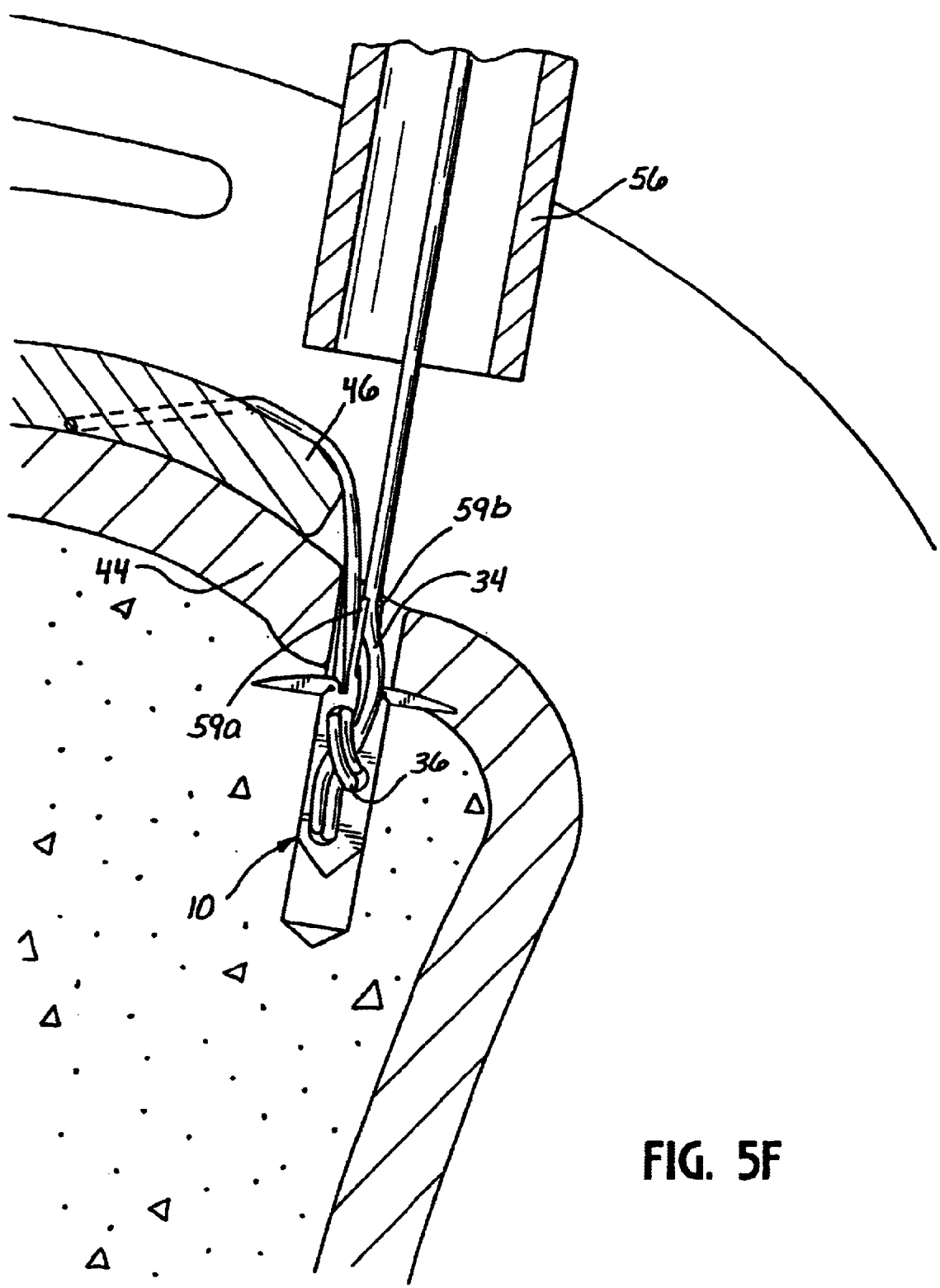
Figure 5G:
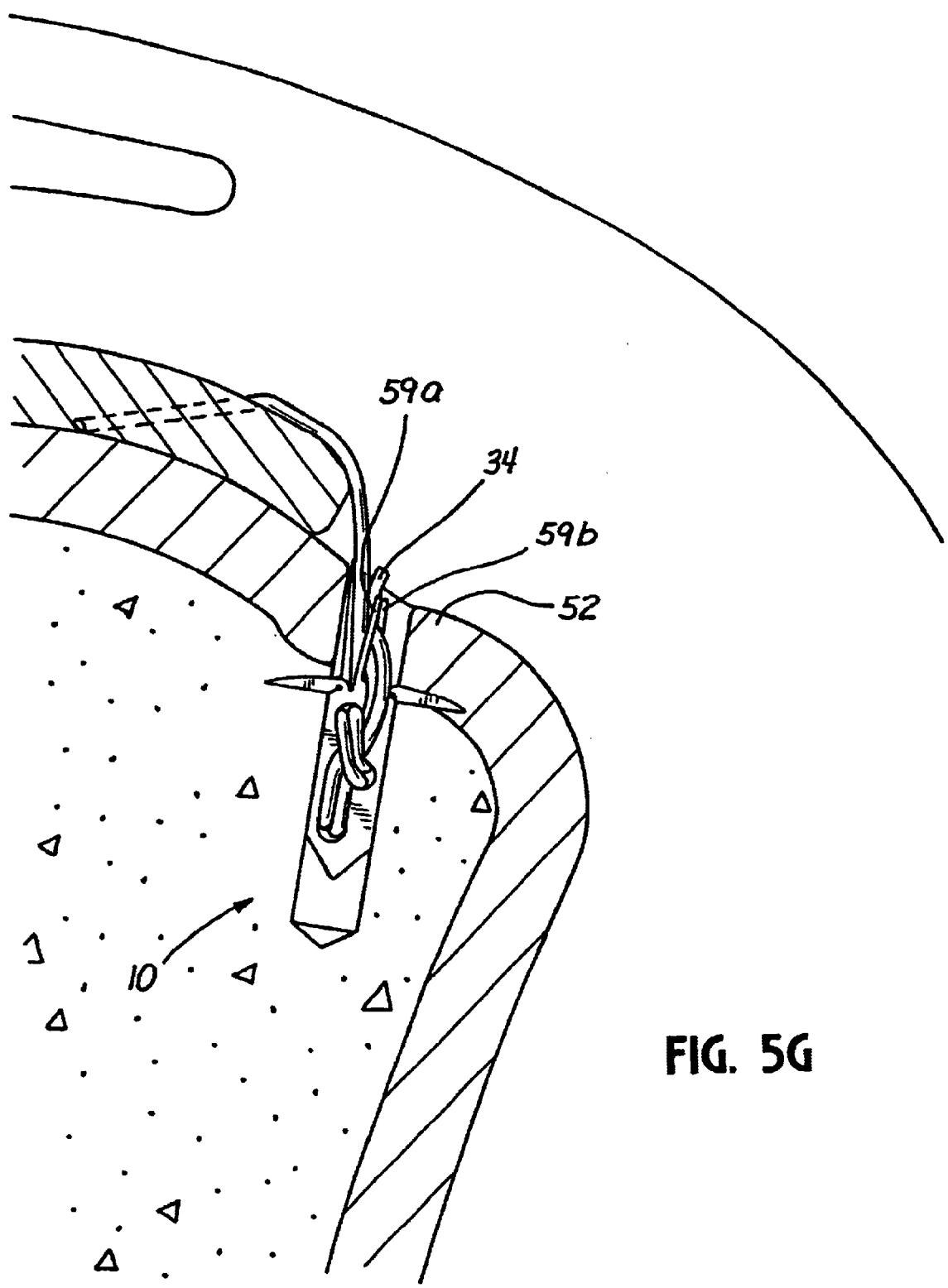

In FIG. 5f additional tension has been applied to the proximal end of the suture 34, and, in comparing the position of the rotator cuff 46 as illustrated in FIGS. 5e and 5f, it may be seen that the rotator cuff 46 has been pulled down against the cortical bone 52 by the manual action of creating tension on the loose legs of the suture 34. This tightening of the suture 34 and the subsequent approximation of the rotator cuff 46 to the bone 52 is made irreversible by the frictional force between the suture 34 passing through the suture loop 36. In order to absolutely assure that the suture 34 may not loosen, the suture 34 is then preferably threaded between two tabs 59a, 59b which have been formed at the proximal end of the bone anchor 10 as a result of the breaking of the weak links 22a,b. Then, as shown in FIG. 5g, the ends of the tabs 59a, 59b may be pinched together tightly against the suture 34 in order to secure the loose ends of the suture 34 to the proximal end of the bone anchor 10 and to prevent any potential loosening or unraveling of the suture 34. The suture 34 may then be cut, as illustrated in FIG. 5g, at the outer edge of the cortical bone 52 and the excess suture removed to complete the inventive procedure.

Figure 5H:
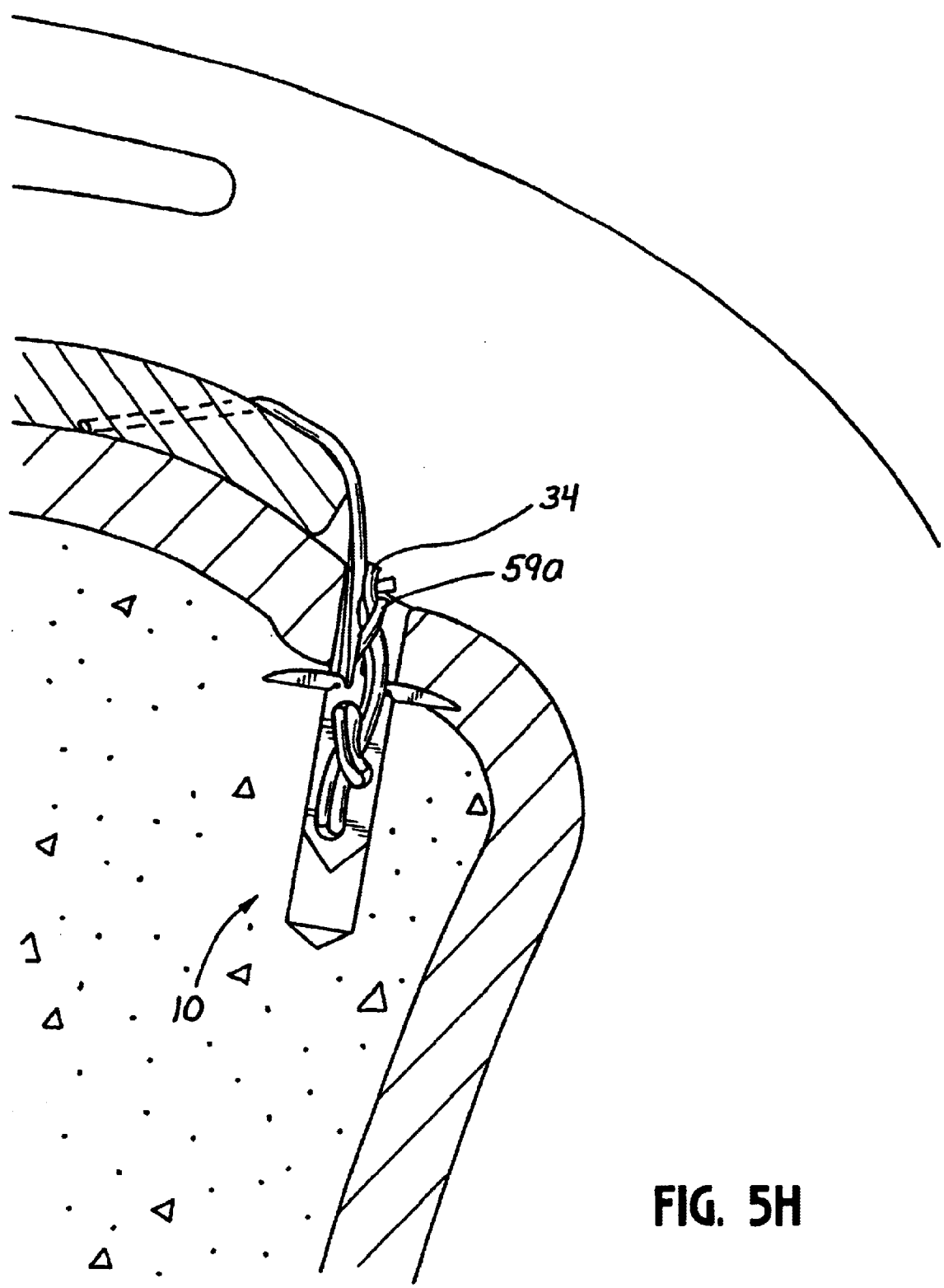
Figure 5I:
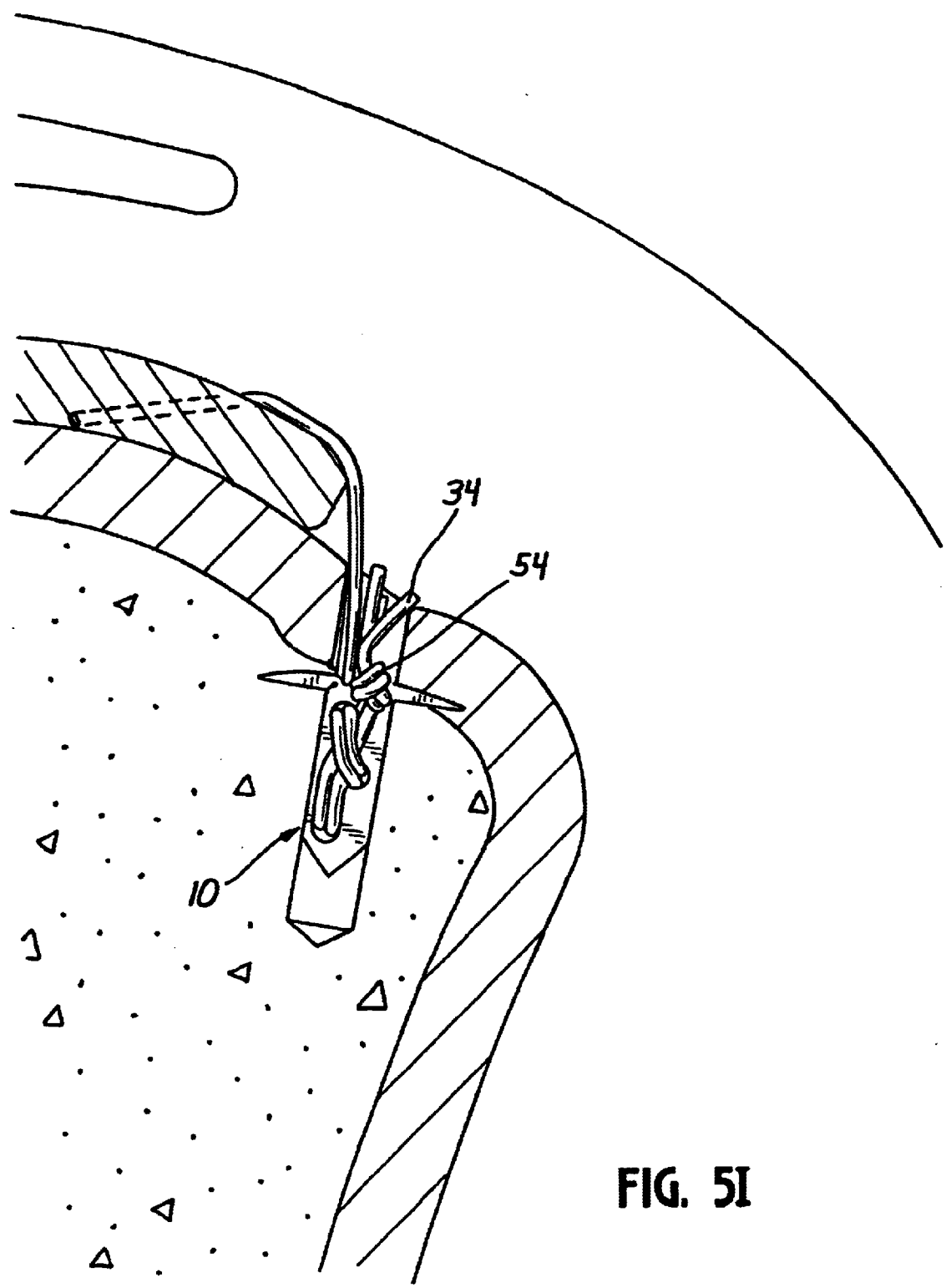
Figure 6:
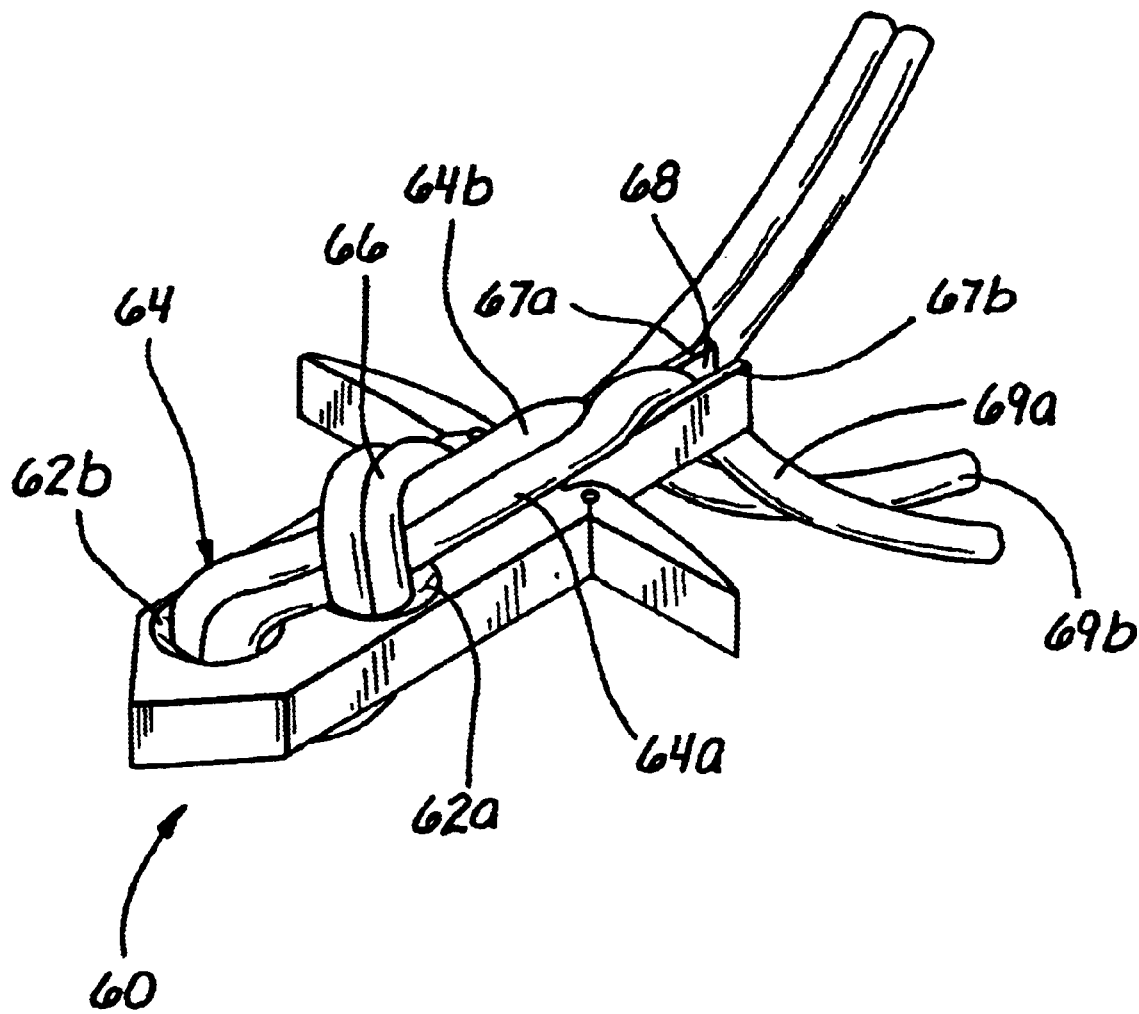
FIG. 6 is a perspective view of an inventive anchoring device of the type shown in FIGS. 1–5I, illustrating one alternative approach for locking the suture in place.

Alternative methods for preventing loosening or unraveling of the suture 34 from the bone anchor 10 are illustrated in FIG. 5h, wherein the tabs 59a, 59b are shown as having been twisted together around the loose ends of the suture 34 (as opposed to being merely pinched together, as shown in FIG. 5g), and in FIG. 5i, wherein a knot 54 is illustrated as having been tied in the suture at the proximal end of the bone anchor 10 (in which's case the tabs 59a, 59b are not required). In FIG. 6, another alternative approach is illustrated, wherein an alternative bone anchor 60 has only two apertures 62a, 62b, as opposed to the three suture retaining apertures illustrated in connection with the earlier embodiments. In this embodiment, a length of suture 64 (which preferably comprises two free legs 64a, 64b) is threaded from the top side of the bone anchor 60 down through the eyelet hole 62a, then up through the eyelet hole 62b, and is passed under a loop 66 between the eyelet hole 62a and the body of the bone anchor 60. At the proximal end of the bone anchor 60 are two tabs 67a, 67b that define a slot 68. Free suture ends 69a, 69b are threaded into the slot 68, which by nature of the shape of the tabs 67 is tapered. As the suture ends 69a, 69b are pulled down into the slot 68 they are wedged and held by frictional force to prevent the sutures from loosening as discussed above.

Figure 7:
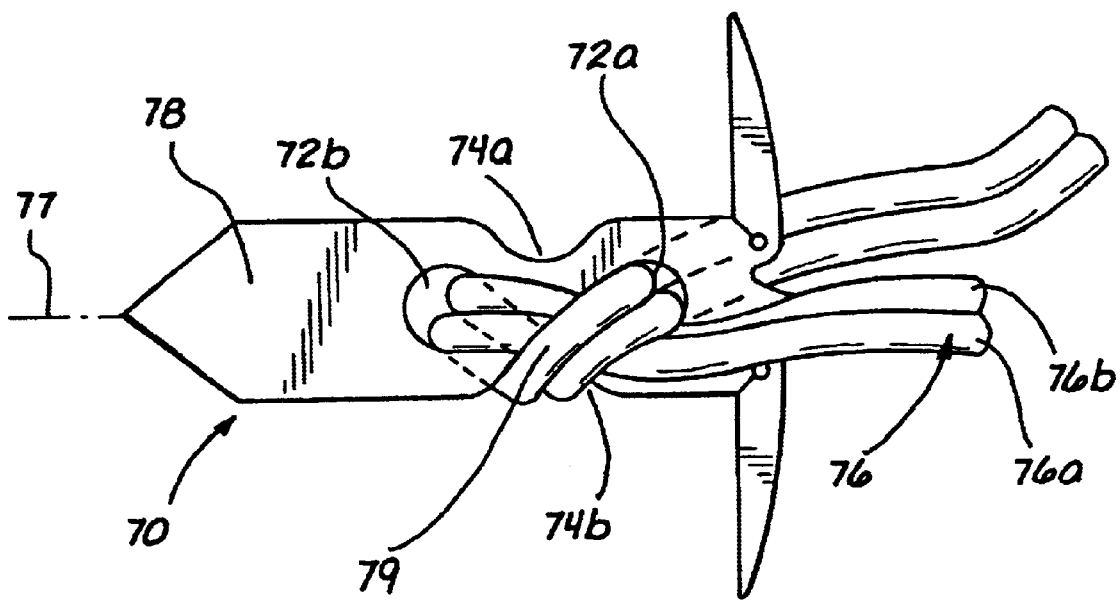
FIG. 7 is a plan view of an alternate embodiment of the inventive bone anchor device.
Figure 8:
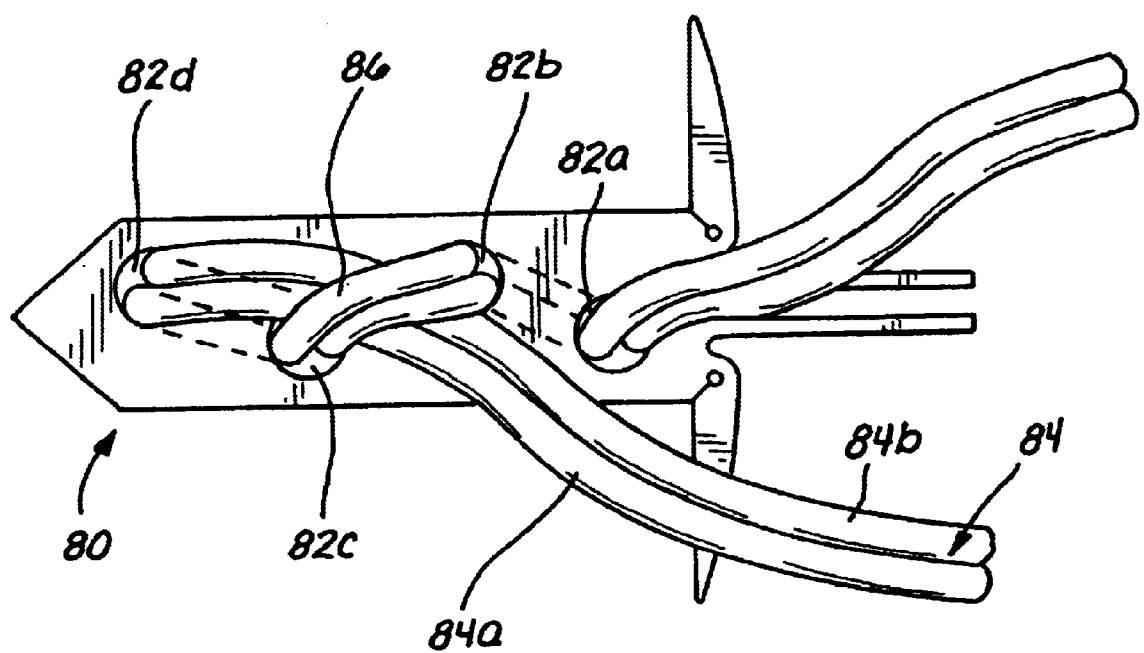
FIG. 8 is a plan view similar to that of FIG. 7, illustrating another alternate embodiment of the inventive device.

Additional alternative embodiments of the present invention may be seen by referring to FIGS. 7–8. FIG. 7 illustrates an alternative bone anchor 70 of the same general shape as that shown in prior embodiments, having two axially spaced eyelet holes 72a, 72b and with the addition of two troughs 74a, 74b forming a waist near the middle section of the bone anchor 70. It will be noted that in this waisted embodiment, the two eyelet holes (or suture retaining apertures) 72a, 72b are axially aligned, meaning that they are both centered on the longitudinal axis 77 of the anchor 70, as opposed to the prior illustrated embodiments, wherein the axially spaced apertures are offset from the longitudinal axis, in staggered fashion. This difference is possible because of the waisted configuration of the anchor body 78, which permits the wrapped suture lengths to achieve the same angled suture orientations as in the prior embodiments.

In this embodiment, a length of suture 76, comprising free legs 76a, 76b, is threaded from the rear side of the bone anchor 70 through the eyelet hole 72a, then weaved about the anchor body 78 through the trough 74b from the front side of the bone anchor 70 and back to the rear side of the anchor body 78. The suture 76 is then threaded through the eyelet hole 72b to the front side of the bone anchor 70 and passed through a loop 79 created between the eyelet hole 72a and the trough 74b. In all respects, the deployment of the bone anchor is essentially the same as with those anchors described above, and it should be clear that the tension in the suture 76 as it passes through the loop 78 creates a binding force similar to that previously described with the 3 hole anchor.

In FIG. 8, an alternative embodiment illustrated as a bone anchor 80 is virtually the same in shape, description and deployment to the preferred embodiment herein described with the exception that there are four eyelet holes 82a, 82b, 82c, and 82d instead of three such eyelet holes. The purpose for discussing this embodiment is to emphasize the general principle that, though three suture retaining apertures are preferred, any number of such apertures may be employed, if desired, within the scope of the present invention. In this figure, a length of suture 84, preferably comprising free legs 84a, 84b, as discussed supra, is threaded from front to rear through eyelet hole 82a, from rear to front through eyelet hole 82b, from front to rear again through eyelet hole 82c, and, finally, threaded from rear to front through eyelet hole 82d. It is then passed through the loop 86 created between eyelet holes 82b and 82c and tension applied as fully described in connection with the preferred embodiment, supra. Again, it is the tension in the suture 84 that creates the binding force in the loop 86.

It is to be understood that the figures of the bone and anchors seen above are purely illustrative in nature, and are not intended to perfectly reproduce the physiologic and anatomic nature of the humeral head as expected to be seen in the human species, nor to limit the application of the inventive embodiments to repair of the rotator cuff. The invention is applicable to many different types of procedures involving, in particular, the attachment of connective or soft tissue to bone.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention. In particular, it is noted that the procedures, while oriented toward the arthroscopic repair of the rotator cuff, are applicable to the repair of any body location wherein it is desired to attach or reattach soft tissue to bone, particularly using an arthroscopic procedure.

What is claimed is:

1. A bone anchor device for attaching connective tissue to bone, comprising:
    an anchor body having a longitudinal axis disposed along a center thereof, and having a proximal end and a distal end;
    a plurality of suture retaining apertures disposed in said anchor body;
    deployable structure for securing said anchor body in bone;
    wherein said plurality of suture retaining apertures are spaced axially relative to one another, in a direction along said longitudinal axis, wherein one of said suture retaining apertures is disposed distally of another of said suture retaining apertures; and
    at least two of said plurality of suture retaining apertures being transversely offset from one another relative to said longitudinal axis.

2. The bone anchor device as recited in claim 1, wherein said plurality of suture retaining apertures comprises two suture retaining apertures.

3. The bone anchor device as recited in claim 1, wherein said plurality of suture retaining apertures comprises three suture retaining apertures.

4. The bone anchor device as recited in claim 1, wherein said plurality of suture retaining apertures comprises four suture retaining apertures.

5. The bone anchor device as recited in claim 1, wherein a first of the at least two of said plurality of suture retaining apertures is disposed on one side of the longitudinal axis and a second of the at least two of said plurality of suture retaining apertures is disposed on the other side of the longitudinal axis.

6. The bone anchor device as recited in claim 1, wherein said deployable structure comprises a pair of deployable flaps.

7. The bone anchor device as recited in claim 1, wherein said anchor body comprises a substantially planar surface in which said plurality of suture retaining apertures are disposed.

8. The bone anchor device as recited in claim 7, wherein said anchor body comprises opposing substantially flat surfaces, said plurality of suture retaining apertures extending through said entire anchor body.

9. The bone anchor device as recited in claim 1, and further comprising a stem extending proximally from a proximal end of said anchor body.

10. The bone anchor device as recited in claim 9, and further comprising a longitudinal slit, at least a portion of which is disposed in said stem.

11. A bone anchor device for attaching connective tissue to bone, comprising:
    an anchor body having opposing substantially flat surfaces;
    deployable structure on said anchor body, such that said deployable structure is disposed closer to a proximal end of said anchor body than to a distal end of said anchor body for securing said anchor body in bone; and
    a plurality of suture retaining apertures extending through said anchor body flat surfaces, said plurality of suture retaining apertures being disposed distally of said deployable structure.

12. A bone anchor device for attaching connective tissue to bone, comprising:
    an anchor body having a distal end and a proximal end, and opposing substantially flat surfaces;
    a stem extending proximally from the proximal end of the anchor body;
    a deployable flap disposed on the proximal end of the anchor body; and
    a notch on said anchor body at a location joining said anchor body and said deployable flap, said notch being adapted to cause said deployable flap to deploy outwardly when force is applied to a proximal end of the deployable flap by a distally moving actuator.

13. A bone anchor device for attaching connective tissue to bone, comprising:
    an anchor body having a distal end and a proximal end;
    a stem extending proximally from the proximal end of the anchor body;
    a deployable flap disposed on the proximal end of the anchor body and spaced from said stem; and
    a slit, at least a portion of which is disposed in said stem;
    said slit forming weak links on opposing sides thereof in said stem, said weak links providing a sole place of weakness in said stem so that when sufficient tensile force is applied to said stem, said weak links fracture first, causing said stem and said anchor body to separate from one another at an axial location coincident with said slit.

14. A bone anchor device for attaching connective tissue to bone, comprising:
    an anchor body having two opposing planar surfaces and having a proximal end and a distal end;

a stem extending proximally from the proximal end of the anchor body;

a first suture retaining aperture disposed in said anchor body and extending through both of said opposing surfaces;

a second suture retaining aperture disposed in said anchor body distally of said first suture retaining aperture;

said first and second suture retaining apertures being transversely offset relative to one another and said longitudinal axis and a length of suturing material extending through each of said suture retaining apertures;

wherein said length of suturing material is looped about said anchor body and contacts substantial portions of both of said two opposing surfaces.

15. The bone anchor device as recited in claim 14, wherein a first portion of the length of suturing material is looped over a second portion of the length of suturing material, the second portion of which lies in contacting engagement with one of said opposing surfaces of said anchor body.

16. A method for securing connective tissue to bone, comprising:

securing a first end of a length of suture to a portion of soft tissue to be attached to a portion of bone;

threading a second end of the length of suture sequentially through a plurality of suture retaining apertures in a body of a bone anchor device, after said securing step has been performed, so that the length of suture is securely fastened to said bone anchor body;

placing said bone anchor body in a blind hole disposed in said portion of bone;

deploying structure on said bone anchor body in an outward direction to secure said bone anchor body in said blind hole; and separating a stem extending proximally from said anchor body from said anchor body.

17. The method as recited in claim 16, and further comprising a step of tensioning said suture, to approximate said portion of soft tissue to said portion of bone.

18. The method as recited in claim 17, and further comprising a step of securing a proximal end of the length of suture to said anchor body.

19. A bone anchor device for attaching connective tissue to bone, comprising:

an anchor body comprising a substantially planar surface;

a plurality of suture retaining apertures disposed on said substantially planar surface of said anchor body; and deployable structure for securing said anchor body in bone.

20. The bone anchor device as recited in claim 19, wherein said anchor body comprises opposing substantially planar surfaces and said plurality of suture retaining apertures extend through said entire anchor body.

21. A bone anchor device for attaching connective tissue to bone, comprising:

an anchor body;

a plurality of suture retaining apertures disposed in said anchor body;

a stem extending proximally from a proximal end of said anchor body;

a longitudinal slit, at least a portion of which is disposed in said stem; and deployable structure disposed on the proximal end of the anchor body and spaced from said stem for securing said anchor body in bone.

* * * * *

UNITED STATES PATENT AND TRADEMARK OFFICE
CERTIFICATE OF CORRECTION

PATENT NO. : 6,652,561 B1
DATED : November 25, 2003
INVENTOR(S) : Tran

It is certified that error appears in the above-identified patent and that said Letters Patent is hereby corrected as shown below:

Column 3,
Line 25, after "a" change "substantialhole" to -- substantial hole --.

Column 6,
Line 56, after "the" delete -- X --.
Line 65, after "24" delete -- em --.
Line 67, after "structure" start a new paragraph with "Referring"

Column 7,
Line 27, after "and" change "11c" to -- 12c --.
Lines 44, 49 and 50, after "angle" change "a" to -- ∝ --.

Column 9,
Line 30, after "in" change "The" to -- the --.

Column 14,
Line 25, after "a" change "stern" to -- stem --.

Signed and Sealed this

Twenty-fifth Day of January, 2005

JON W. DUDAS
*Director of the United States Patent and Trademark Office*